United States Patent
Cauley, III et al.

(10) Patent No.: US 11,998,883 B2
(45) Date of Patent: *Jun. 4, 2024

(54) MAGNETIC MIXING APPARATUS

(71) Applicant: TALIS BIOMEDICAL CORPORATION, Chicago, IL (US)

(72) Inventors: Thomas H. Cauley, III, Redwood City, CA (US); David A. Rolfe, San Francisco, CA (US)

(73) Assignee: Talis Biomedical Corporation, Chicago, IL (US)

( * ) Notice: Subject to any disclaimer, the term of this patent is extended or adjusted under 35 U.S.C. 154(b) by 813 days.

This patent is subject to a terminal disclaimer.

(21) Appl. No.: 16/761,005

(22) PCT Filed: Sep. 12, 2018

(86) PCT No.: PCT/US2018/050725
§ 371 (c)(1),
(2) Date: May 1, 2020

(87) PCT Pub. No.: WO2019/190589
PCT Pub. Date: Oct. 3, 2019

(65) Prior Publication Data
US 2021/0008513 A1    Jan. 14, 2021

Related U.S. Application Data

(63) Continuation of application No. 16/029,216, filed on Jul. 6, 2018, now Pat. No. 10,610,843.
(Continued)

(51) Int. Cl.
*B01F 33/452*    (2022.01)
*C12M 1/00*    (2006.01)
(Continued)

(52) U.S. Cl.
CPC ........... *B01F 33/452* (2022.01); *C12M 27/02* (2013.01); *C12M 47/06* (2013.01); *C12N 1/06* (2013.01)

(58) Field of Classification Search
CPC ..... B01F 33/452; B01F 35/212; C12M 27/02; C12M 47/06; C12N 1/06
See application file for complete search history.

(56) References Cited

U.S. PATENT DOCUMENTS

| 2,350,534 A | 6/1944 | Rosinger |
| 2,982,132 A | 5/1961 | Mendlowitz |

(Continued)

FOREIGN PATENT DOCUMENTS

| CN | 102500267 A | 6/2012 |
| CN | 103184143 A | 7/2013 |

(Continued)

OTHER PUBLICATIONS

Gorkin, Robert, et al. "Pneumatic pumping in centrifugal microfluidic platforms." Microfluidics and nanofluidics 9.2 (2010): 541-549. (Year: 2010).*

(Continued)

*Primary Examiner* — Louise W Humphrey
*Assistant Examiner* — Candice Lee Swift
(74) *Attorney, Agent, or Firm* — Shay Glenn LLP

(57) ABSTRACT

This disclosure relates to a magnetic mixing apparatus that mixes a sample contained in a mixing chamber using a stir bar, while minimizing the amount of contact between the stir bar and walls of the mixing chamber. In one aspect, the apparatus comprises a ferromagnetic stir bar contained in the mixing chamber, and a driving magnet and a driven magnet located on opposite sides of the mixing chamber. The driving magnet, the driven magnet, and the ferromagnetic stir bar are each capable of rotating about a respective axis.

(Continued)

The driving magnet, the driven magnet, and the ferromagnetic stir bar are magnetically coupled such that rotation of the driving magnet induces rotation of the driven magnet and rotation of the driving magnet and the driven magnet induce rotation of the ferromagnetic stir bar. In some embodiments, rotation of the ferromagnetic stir bar within the mixing chamber mixes the sample contained within the mixing chamber.

21 Claims, 10 Drawing Sheets

Related U.S. Application Data

(60) Provisional application No. 62/591,370, filed on Nov. 28, 2017.

(51) Int. Cl.
  *C12M 1/06* (2006.01)
  *C12N 1/06* (2006.01)

(56) References Cited

U.S. PATENT DOCUMENTS

| | | | |
|---|---|---|---|
| 2,990,256 | A | 6/1961 | Lovins |
| 3,211,433 | A | 10/1965 | Chrostowski et al. |
| 3,570,819 | A | 3/1971 | Rosinger |
| 6,357,907 | B1 | 3/2002 | Cleveland et al. |
| 6,416,215 | B1 | 7/2002 | Terentiev |
| 6,517,231 | B1 | 2/2003 | Biardeau et al. |
| 6,663,276 | B2 | 12/2003 | Yale |
| 7,075,040 | B2 | 7/2006 | McFadden et al. |
| 7,484,880 | B2 | 2/2009 | Cleveland et al. |
| 7,855,069 | B2 | 12/2010 | Lee et al. |
| 8,222,023 | B2 | 7/2012 | Battrell et al. |
| 8,399,190 | B2 | 3/2013 | Belgrader et al. |
| 8,434,930 | B2 | 5/2013 | Huhta |
| 9,174,210 | B2 | 11/2015 | Selden et al. |
| 9,333,471 | B2 | 5/2016 | Carrera Fabra et al. |
| 9,574,225 | B2 | 2/2017 | Himmelreich et al. |
| 9,580,679 | B2 | 2/2017 | Njoroge et al. |
| 9,956,534 | B2 | 5/2018 | Hammerschmidt et al. |
| 10,610,843 | B2 | 4/2020 | Cauley et al. |
| 2001/0039369 | A1 | 11/2001 | Terentiev |
| 2014/0192613 | A1 | 7/2014 | Terentiev |
| 2016/0023204 | A1 | 1/2016 | Schaff et al. |
| 2016/0346781 | A1 | 12/2016 | Shen et al. |

FOREIGN PATENT DOCUMENTS

| | | | | |
|---|---|---|---|---|
| CN | 104285143 | A | | 1/2015 |
| EP | 1731217 | A1 | | 12/2006 |
| WO | WO93/07388 | A1 | | 4/1993 |
| WO | WO96/022630 | A1 | | 7/1996 |
| WO | WO96/041080 | A1 | | 12/1996 |
| WO | WO02/031372 | A1 | | 4/2002 |
| WO | WO02/036253 | A2 | | 5/2002 |
| WO | WO2013/156199 | A1 | | 10/2013 |
| WO | WO-2018014031 | A1 | * | 1/2018 ............. B01F 13/08 |

OTHER PUBLICATIONS

Khalil, Islam SM, et al. "Rubbing against blood clots using helical robots: Modeling and in vitro experimental validation." IEEE Robotics and Automation Letters 2.2 (2017): 927-934. (Year: 2017).*

Andersson, Helene, et al. "Micromachined flow-through filter-chamber for chemical reactions on beads." Sensors and Actuators B: Chemical 67.1-2 (2000): 203-208. (Year: 2000).*

Klimek-Ochab, Magdalena, et al. "Comparative study of fungal cell disruption—scope and limitations of the methods." Folia microbiologica 56 (2011): 469-475. (Year: 2011).*

Research Products International; https://www.rpicorp.com/products/laboratory-equipment/labware/flea-micro-magnetic-stirring-bar-7-x-2-mm.html; accessed Mar. 17, 2023 (Year: 2023).*

Beckman Coulter; https://www.beckman.com/reagents/genomic/cleanup-and-size-selection/; accessed Mar. 17, 2023 (Year: 2023).*

Fisher Scientific; https://www.fishersci.com/shop/products/100um-low-bind-zirconium-beads/NC1147014; accessed Mar. 17, 2023 (Year: 2023).*

Yan et al.; Multiplex detection of bacteria on an integrated centrifugal disk using bead-beating lysis and loop-mediated amplification; Scientific Reports; 7(1460); pp. 1-11; May 3, 2017.

* cited by examiner

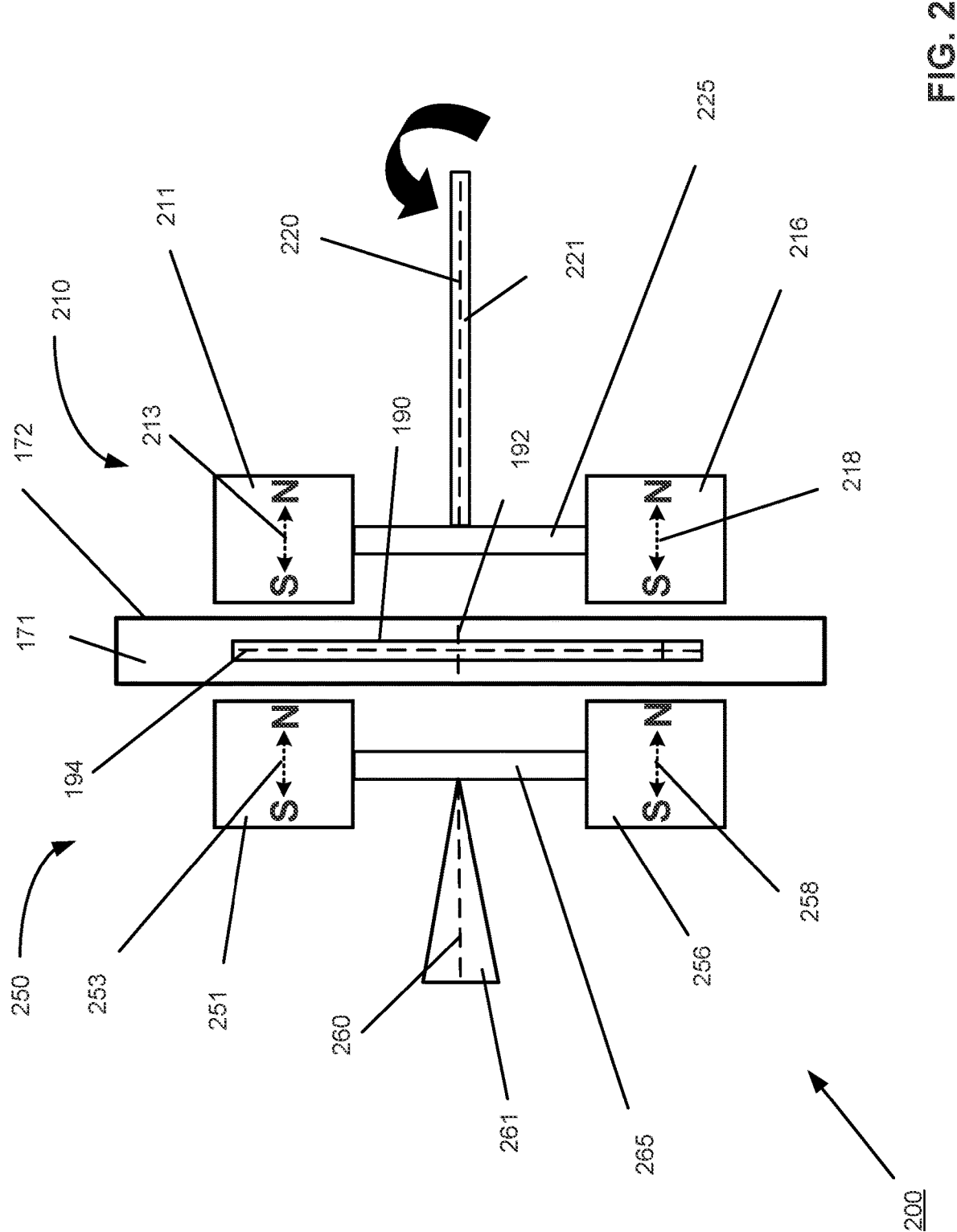

MAGNETIC MIXING APPARATUS

CROSS-REFERENCE TO RELATED APPLICATIONS

This application claims the benefit of and priority to U.S. Provisional Application No. 62/591,370, filed on Nov. 28, 2017, and U.S. Non-Provisional patent application Ser. No. 16/029,216, filed on Jul. 6, 2018, both of which are incorporated by reference in their entirety.

STATEMENT REGARDING FEDERALLY SPONSORED RESEARCH OR DEVELOPMENT

This invention was made with government support under contract number HR0011-11-2-0006 awarded by the Department of Defense (DARPA). The government has certain rights in the invention.

TECHNICAL FIELD

The present invention relates to the field of magnetic mixing systems and cell lysis. In particular, the present disclosure is directed toward systems, devices, and methods for mixing a sample and/or lysing cells within a mixing chamber using a stir bar, minimizing the interaction of the stir bar with walls of the mixing chamber.

BACKGROUND

Many steps in biological methods require mixing of different solutions together, e.g. a cellular sample with an intent of cell lysis. In the laboratory, this mixing typically is performed manually using a vortex mixer on a laboratory benchtop. However, vortex mixing is difficult to implement on a consumable, point-of-care diagnostic device because diffusion is not sufficient for small quantities of fluid, for viscous solutions, and for solutions of differential densities.

An alternative method for mixing different solutions together uses a magnetic stir plate and a magnetic stir bar capable of rotation. However, forceful contact of the stir bar with walls of a mixing container in which the stir bar is contained during rotation can result in damage to the walls of the container or to the stir bar, as well as contamination of the sample.

SUMMARY

The present disclosure relates generally to a magnetic mixing apparatus that mixes a sample contained in a mixing chamber using a stir bar, while minimizing the amount of contact of the stir bar with walls of the mixing chamber.

In an aspect, the disclosure provides a magnetic mixing apparatus that comprises a driving magnet system, a drive motor, a driven magnet system, a gap separating the driving magnet system and the driven magnet system, a stationary mixing assembly disposed within the gap, and a stir bar. In some embodiments, the driving magnet system comprises one or more driving magnets. In further embodiments, the driving magnet system is configured to rotate about a driving magnet rotational axis. The driving magnet system can be operably and/or mechanically coupled to the drive motor, and the drive motor is capable of driving rotation of the driving magnet system about the driving magnet rotational axis. In certain embodiments, the driven magnet system comprises one or more driven magnets. In further embodiments, the driven magnet system is configured to rotate about a driven magnet rotational axis. The arrangement of the driven and driving magnet systems across the gap effectuates a magnetic coupling between each driving magnet and a corresponding driven magnet whereby rotation of the driving magnet system about the driving magnet rotational axis induces rotation of the driven magnet system about the driven magnet rotational axis. The stationary mixing assembly can comprise a mixing chamber having a mixing chamber volume surrounded by a bounding surface. The stir bar can be contained within the mixing chamber volume. In some embodiments, the stir bar can comprise a stir bar volume and a ferromagnetic material. Disposition of the stir bar between the driving magnet system and the driven magnet system can create a low-reluctance magnetic circuit and effectuate a magnetic coupling between the stir bar, at least one of the one or more driving magnets, and at least one of the one or more driven magnets, whereby rotation of the driving magnet system about the driving magnet rotational axis and rotation of the driven magnet system about the driven magnet rotational axis induces rotation of the stir bar about a stir bar rotational axis.

In certain aspects, at least one of the one or more driving magnets has a magnetic axis aligned to a magnetic axis of one of the one or more driven magnets, such that the magnets are attracted to one another. In a further aspect, the stir bar is attracted to the driving magnet system and to the driven magnet system.

In some embodiments, the one or more driving magnets are mounted in a driving magnet holder configured to rotate about the driving magnet rotational axis. In further embodiments, a driving magnet spindle is operably coupled to the driving magnet holder and to the drive motor. The driving magnet spindle can be substantially collinear with the driving magnet rotational axis. In such embodiments, the drive motor can be capable of driving rotation of the driving magnet holder about the driving magnet rotational axis. In one embodiment, the driving magnet system can comprise a single driving magnet. In such embodiments, a largest dimension of the single driving magnet can be perpendicular to the driving magnet axis of rotation. In an alternative embodiment, the driving magnet system can comprise 2 driving magnets separated by a distance that transects the rotational axis of the driving magnet. Typically a driving magnet holder will maintain the two driving magnets in a fixed geometry relative to one another.

In additional embodiments, the one or more driven magnets are mounted in a driven magnet holder configured to rotate about the driven magnet rotational axis. In such embodiments, a driven magnet spindle can be operably coupled to the driven magnet holder. In further embodiments, the driven magnet spindle can be substantially collinear with the driven magnet rotational axis. In one embodiment, the driven magnet system can comprise a single driven magnet. In such embodiments, a largest dimension of the single driven magnet can be perpendicular to the driven magnet axis of rotation. In an alternative embodiment, the driven magnet system can comprise 2 driven magnets separated by a distance that transects the driven magnet rotational axis. Typically a driven magnet holder will maintain the two driven magnets in a fixed geometry relative to one another.

In some embodiments, the one or more driving and driven magnets are neodymium magnets. In certain implementations, the residual flux density of the driving magnet system is between 5000 and 40000 Gauss and the residual flux density of the driven magnet system is between 5000 and 40000 Gauss. In further embodiments, the gap separating the driving magnet system and the driven magnet system can be 10-30 mm.

In some embodiments, the ferromagnetic material of the stir bar is ferritic stainless steel or duplex stainless steel. In further embodiments, the stir bar comprises a permanent magnet. In additional embodiments, a relative magnetic permeability of the stir bar can be between 500-1,000,000. In certain embodiments, the stir bar is positioned within the mixing chamber such that a plane of rotation of the stir bar is substantially equidistant from the driving magnet system and the driven magnet system.

In some embodiments, the mixing assembly can be disposed within the gap such that the driving magnet rotational axis, the driven magnet rotational axis, and the stir bar rotational axis are substantially collinear and such that the stir bar makes little contact with the bounding surface of the mixing chamber. The stationary mixing assembly can be retained within a mixing assembly holder in certain embodiments. In some embodiments, the mixing assembly is disposable.

In certain embodiments, the mixing chamber volume and the stir bar volume are proportioned such that the stir bar makes little contact with the bounding surface of the mixing chamber. For instance, the mixing chamber volume can comprise 0.1 mL-100 mL in some embodiments. The stir bar volume can comprise 50 uL-10 mL in some embodiments.

In some embodiments, a largest dimension of the mixing chamber and a largest dimension of the stir bar are proportioned such that the stir bar makes little contact with the bounding surface of the mixing chamber. In such embodiments, the largest dimension of the mixing chamber volume can comprise 1 mm-200 mm. In additional embodiments, the largest dimension of the stir bar volume is 0.5 mm-180 mm.

In some embodiments, the magnetic mixing apparatus further comprises one or more field focusers coupled to at least one of the one or more driving magnets and the one or more driven magnets, the field focusers positioned to focus magnetic fields generated by the driving magnet system and the driven magnet system towards a narrow radial segment along a largest dimension of the driving and driven magnetic systems. In some embodiments, beads can be contained within the mixing chamber volume.

In certain embodiments, the magnetic mixing apparatus can further comprise an acoustic mechanism for detecting magnetic decoupling of the stir bar from one or more of the driving magnet system and the driven magnet system. In such embodiments, the acoustic mechanism is configured to detect a change in one or more of an amplitude and a frequency of vibrations produced by the stir bar during rotation of the driving magnet system, the change indicating the magnetic decoupling of the stir bar. In some embodiments, the change comprises a sudden decrease in one or more of the amplitude and the frequency of the vibrations produced by the stir bar. In some embodiments, the acoustic mechanism comprises a microphone.

In another aspect, the disclosure provides methods of lysing a cell using chemical methods. The methods can comprise introducing a sample comprising a cell into the mixing chamber described above, providing a solution comprising one or more chemical lysing agents, and energizing the drive motor, whereby energizing the drive motor sufficiently rotates the stir bar to mix the sample with the chemical solution within the mixing chamber and thereby promote cell lysis. In such embodiments, cell lysis can be promoted by adding beads to the mixing chamber, as described above.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale; the size and relative sizes of components may be exaggerated for clarity. Like numbers refer to like elements throughout. In the drawings:

FIG. 2 is a profile view of a schematic diagram of a magnetic mixing apparatus including a di-lithic driving magnet and a di-lithic driven magnet, in accordance with an embodiment.

DETAILED DESCRIPTION

Figure 1:
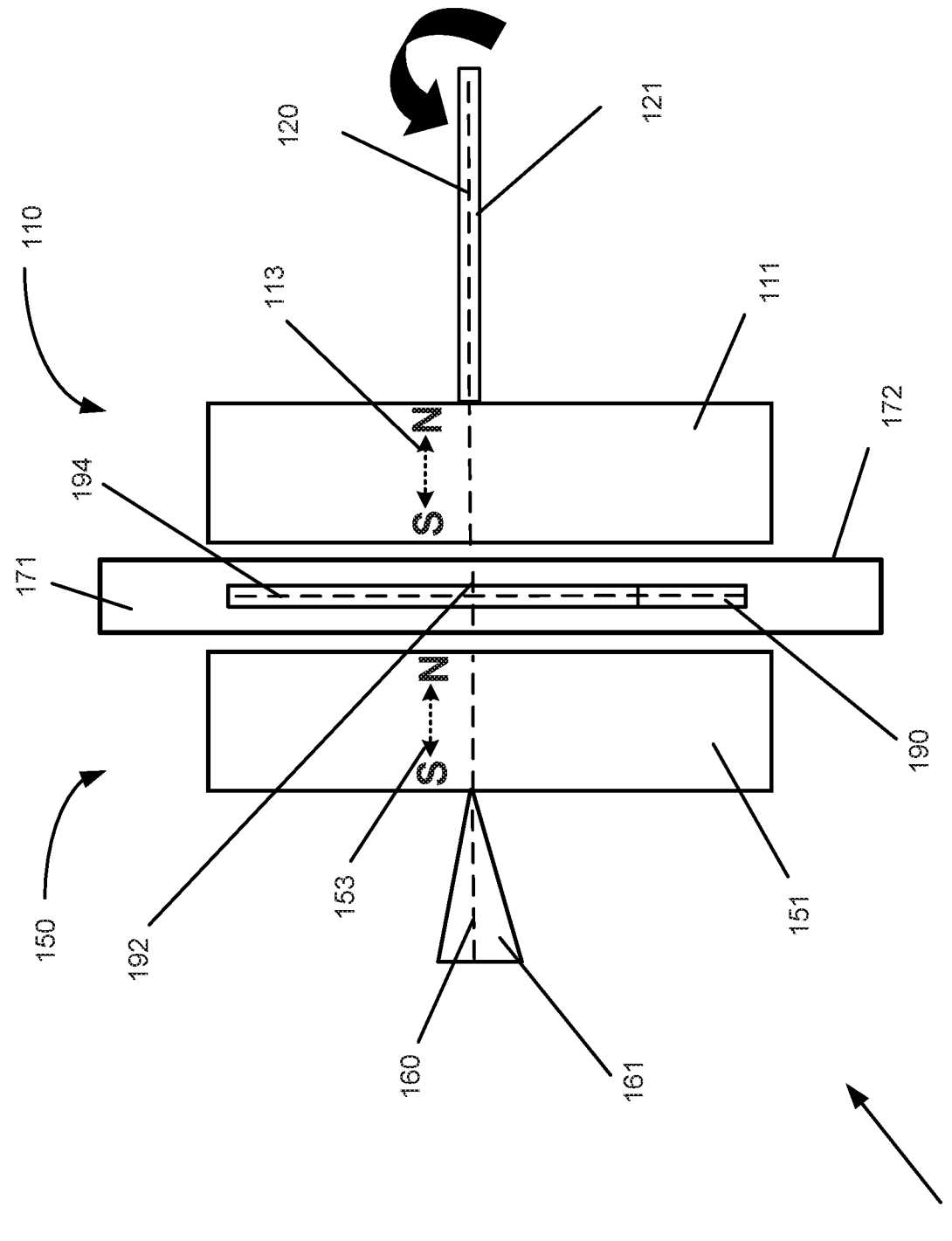
FIG. 1 is a profile view of a schematic diagram of a magnetic mixing apparatus, in accordance with an embodiment.

Systems, devices, and methods for mixing a sample contained in a mixing chamber using a stir bar, while minimizing the amount of contact between the stir bar and a surface bounding the mixing chamber ("bounding surface"), are provided herein. The methods include introducing the sample into the mixing chamber containing a ferromagnetic stir bar, rotating a driving magnet system located on one side of the mixing chamber, inducing rotation of a driven magnet system located on an opposite side of the mixing chamber, and inducing rotation of the ferromagnetic stir bar, thereby mixing the sample.

Before the disclosed embodiments are described in greater detail, it is to be understood that this disclosure is not limited to particular embodiments described, as such can, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges can independently be included in the smaller ranges and are also encompassed within the present disclosure, subject to any specifically excluded limit in the stated range. Where the stated range includes one or both of the limits, ranges excluding either or both of those included limits are also included in the present disclosure.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which these disclosed embodiments belong. Although any methods and materials similar or equivalent to those described herein can also be used in the practice or testing of the disclosed embodiments, representative illustrative methods and materials are now described. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It is noted that, as used herein and in the appended claims, the singular forms "a," "an," and "the" include plural referents unless the context clearly dictates otherwise.

Systems

Included in the disclosure are systems, devices, and methods for mixing a sample contained in a mixing chamber using a stir bar, while minimizing the amount of contact between the stir bar and walls of the mixing chamber. Systems according to the subject embodiments include a driving magnet system, a driven magnet system, and a ferromagnetic stir bar contained within a mixing chamber used in conjunction with one another to mix a sample. Ferromagnetism is the quality of being able to induce a dipole in a magnetic field.

FIG. 1 is a profile view of a schematic diagram of a magnetic mixing apparatus 100, in accordance with an embodiment. The magnetic mixing apparatus includes a driving magnet system 110 comprising one or more driving magnets, a driven magnet system 150 comprising one or more driven magnets, and a mixing chamber 171. The mixing chamber is disposed within a gap between the driving magnet system and the driven magnet system. The mixing chamber comprises a bounding surface 172 and contains a stir bar 190. Typically, but not necessarily, the driving magnet system and driven magnet system will each contain the same number of magnets. Similarly, typically the magnets will be arranged with the driving and driven magnet systems such that each magnet in the driven magnet system will be located directly, or nearly directly, across the gap from the corresponding magnet in the driving magnet system.

In some embodiments, the driving magnet system and/or the driven magnet system comprise a single, monolithic magnet. For instance, in the embodiment depicted in FIG. 1, the driving magnet system comprises a single driving magnet 111 and the driven magnet system comprises a single driven magnet 151. In alternative embodiments, the driving magnet system and/or the driven magnet system can comprise a plurality of magnets. For example, in the embodiment shown in FIG. 2 and discussed in greater detail below, the driving magnet system and the driven magnet system each comprise two magnets or more.

As shown in FIG. 1, the driving magnet comprises a driving magnet magnetic axis 113. The driven magnet also comprises a magnetic axis, referred to as the driven magnet magnetic axis 153. As used herein the term "magnetic axis" refers to a line through the center of a magnet such that torque exerted on the magnet by a magnetic field in the direction of the line is zero. A magnet will have its own magnetic axis. A magnetic system comprised of more than one magnet also will have its own composite magnetic axis, such that torque exerted on the magnetic system as a whole by a magnetic field in the direction of the line is zero. For visualization, FIG. 1 illustrates the magnetic axes 113 and 153 as separate, but parallel, from the rotations axes 120 and 160, respectively. Frequently, for magnetic systems comprised of a single monolithic magnet, the magnetic axis of the monolithic magnet will be substantially collinear with the rotational axis of that magnet.

In a preferred embodiment, a shape of the driving magnet is the same as a shape of the driven magnet. In an even further preferred embodiment, dimensions of the driving magnet are the same as dimensions of the driven magnet. For example, as shown in the embodiment depicted in FIG. 1, a shape of the driving magnet and a shape of the driven magnet can be a rectangular prism. In a further preferred embodiment, a largest dimension of the driving magnet is in a plane perpendicular to the driving magnet magnetic axis and a largest dimension of the driven magnet is in a plane perpendicular to the driven magnet magnetic axis. In a further preferred embodiment, a shortest dimension of the driving magnet is orthogonal to the largest dimension of the driving magnet and a shortest dimension of the driven magnet is orthogonal to the largest dimension of the driven magnet. In a preferred embodiment, the ratio of the largest dimension to the shortest dimension of the driving magnet and/or of the driven magnet is between 20 and 5.

The driving magnet system and the driven magnet system are arranged to effectuate a magnetic coupling between the one or more driving magnets and the one or more driven magnets. Specifically, each driving magnet and driven magnet are arranged with respect to one another such that an alignment of the driving magnet magnetic axis and an alignment of the driven magnet magnetic axis effectuate a magnetic coupling between the driving magnet and the driven magnet. In certain embodiments, to effectuate magnetic coupling between a driving magnet and driven magnet, the driven magnet magnetic axis is parallel to the driving magnet magnetic axis. In further, preferred embodiments, the driven magnet magnetic axis is substantially collinear with the corresponding driving magnet magnetic axis. As used herein, "substantially collinear" encompasses deviations from absolute collinearity of up to 10° and/or 3 mm at a plane bisecting the gap between the driving and driven magnet system.

The magnetic coupling between the driving magnet system and the driven magnet system comprises an attractive magnetic coupling. In such embodiments, the one or more driving magnets and the one or more driven magnets are arranged with respect to one another such that the alignment of the each driving magnet magnetic axis and the alignment of the each driven magnet magnetic axis effectuate an attractive magnetic coupling between the one or more driving magnets and the one or more driven magnets. In general, to effectuate an attractive magnetic coupling between a driving magnet and a driven magnet, the driving magnet magnetic axis and the driven magnet magnetic axis are aligned such that opposing poles of the driving magnet magnetic axis and the driven magnet magnetic axis are located in proximity to one another. For example, as shown in FIG. 1, to effectuate an attractive magnetic coupling between the driving magnet and the driven magnet, a first pole (e.g., a south pole) of the driving magnet magnetic axis is located in proximity to a second, opposing pole (e.g., a north pole) of the driven magnet magnetic axis. In alternative embodiments (not shown), to effectuate an attractive magnetic coupling between the driving magnet and the driven magnet, the second pole (e.g., the north pole) of the driving magnet magnetic axis is located in proximity to the first, opposing pole (e.g., the south pole) of the driven magnet magnetic axis.

In certain embodiments, a strength of the magnetic coupling between the driving magnet system and driven magnet system is based on a distance of the gap located between the one or more driving magnets and the corresponding one or more driven magnets. Additionally, the magnetic coupling is based on a magnet strength of the one or more driving magnets, as well as a magnet strength of the one or more driven magnets. In some embodiments, the gap separating a driving magnet and driven magnet is between about 10 mm and about 30 mm. In a further embodiment, the residual flux density of the driving magnet system is between 5000 and 40000 Gauss and the residual flux density of the driven magnet system is between 5000 and 40000 Gauss. In a preferred embodiment, the magnet strength of the one or more driving magnets is the same as the magnet strength of the one or more driven magnets.

As mentioned above, the mixing chamber is disposed within the gap between the driving magnet system and the driven magnet system. In a preferred embodiment, the mixing chamber is disposed within the gap such that the center, or midpoint, of the mixing chamber is located approximately an equal distance from the driving magnet system and from the driven magnet system. The mixing chamber has a mixing chamber volume. The bounding surface surrounds the mixing chamber volume.

At least one stir bar is contained within the mixing chamber volume. The stir bar can comprise any shape and/or volume. For example, the shape of the stir bar can be selected from a group consisting of cylindrical, spherical, and triangular-prism-shaped. The stir bar frequently has a largest dimension 194 in a plane perpendicular to a stir bar rotational axis 192. The stir bar also has a shortest dimension orthogonal to the largest dimension. In a preferred embodiment, the ratio of the largest dimension to the shortest dimension of the stir bar is between 20 and 5. In some implementations, the stir bar can be an X-shaped stir bar that essentially is a composite of two rod-shaped bars, each having a largest dimension and a narrower shortest dimension orthogonal to the largest dimension. Such an X-shaped stir bar can be used with driving and driven magnet systems containing one, two or four magnets each. In alternative embodiments, a shape of the stir bar can be selected from any other 3-dimensional shape not explicitly disclosed herein.

In some embodiments, the stir bar comprises a ferromagnetic material. For example, the stir bar can comprise ferritic stainless steel or duplex stainless steel. A ferromagnetic material is a material that exhibits susceptibility to magnetization in the presences of a magnetic field. The magnetization may or may not persist after removal of the magnetic field. In certain embodiments, the stir bar has a relative magnetic permeability of between 500-1,000,000. In an embodiment in which a magnetic field travels through a ferromagnetic material, the magnetic domains of the material align within the magnetic field creating an area of low magnetic permeability, where the magnetic field can easily travel. The magnetic flux follows the path of least resistance through the ferromagnetic material, and may realign ferromagnetic material in order to minimize reluctance. Optionally, the stainless steel can be passivated, which removes free iron from the surface of the bar, thus lowering the risk of oxidation.

The stir bar can be encapsulated in an impermeable material corrosion resistance. One of ordinary skill in the art would be able to select an appropriate impermeable material that would not interfere with magnetic flux through the stir bar. Example materials include, but are not limited to PTFE, parylene C, parylene D, functionalized perfluoropolyethers (PFPEs), FEP, Xylan Fluoropolymer, epoxy, and urethane. Similarly, the impermeable material can be applied to the stir bar by any method known in the art, such as by tumble coating. In one implementation, the ferromagnetic material of the stir bar is passivated prior to coating. In a preferred implementation, the stir bar is tumble-coated with a layer of parylene C between 20 µm and 200 µm thick.

By placing the ferromagnetic stir bar within the mixing chamber located in the gap between the driving magnet system and the driven magnet system, a magnetic dipole can be induced across the stir bar. This dipole of the stir bar effectuates a magnetic coupling between the stir bar, the one or more driving magnets, and the one or more driven magnets. Specifically, the introduction of the stir bar into the magnetic field causes the stir bar to be attracted to the one or more driving magnets and the one or more driven magnets. In preferred embodiments in which a magnetic strength of the corresponding driving magnet equals a magnetic strength of the driven magnet, and the driving magnet magnetic axis is substantially collinear with the driven magnet magnetic axis, attraction of the stir bar to the driving magnet and driven magnet causes the stir bar to be located roughly equidistant from driving magnet and driven magnet. In an even further preferred embodiment in which a center of the mixing chamber is located an equal distance from the driving magnet system and the driven magnet system, as a result of the attractive forces between the stir bar and the one or more driving magnets and the stir bar and the one or more driven magnets, the stir bar can be centered within the mixing chamber thereby minimizing the amount of contact between the stir bar and the bounding surface.

Additionally, as discussed above, the stir bar aligns within the magnetic fields generated by the driving magnet system and the driven magnet system such that areas of the magnetic fields with the greatest magnetic field strengths travel through the greatest volume of the stir bar possible. In areas in which the magnetic fields generated by the driving magnet system and the driven magnet system overlap, the overall magnetic field produced as a result of this overlap comprises a magnetic field with parallel magnetic field lines. Specifically, in areas in which the magnetic fields generated by the a driving magnet and driven magnet overlap, the magnetic field produced consists of parallel magnetic field lines traveling from the driving magnet to the driven magnet, and from the driven magnet to the driving magnet. The stir bar aligns within the mixing chamber such that the stir bar is maximally permeated by these parallel magnetic field lines. Thus, the stir bar aligns within the mixing chamber such that the driving magnet magnetic axis and the driven magnet magnetic axis are parallel to and pass through the largest dimension of the stir bar permitted by the boundaries of the mixing chamber.

Because of the shape of the magnet systems, the magnetic field is strongest along the largest dimension of the driving magnet system and the driven magnet system. The magnetic field strength drops rapidly when moving outward in a direction parallel to the shortest dimension of the magnet system. The ferromagnetic stir bar is pulled toward the position which allows the highest magnetic flux to pass through its highly-permeable volume. The torque which causes the stir bar to turn in response to the turning of the driving and driven magnet systems is approximately proportional to the gradient to the magnetic field traveling through the stir bar.

In some embodiments, the driving magnet system is configured to rotate about a driving magnet rotational axis 120. As shown in FIG. 1, the driving magnet rotational axis typically is parallel to the driving magnet magnetic axis. In further, preferred embodiments, the driving magnet rotational axis can be substantially collinear with the driving magnet magnetic axis. In a preferred embodiment, the driving magnet system is symmetric with respect to the driving magnet rotational axis.

Figure 3B:
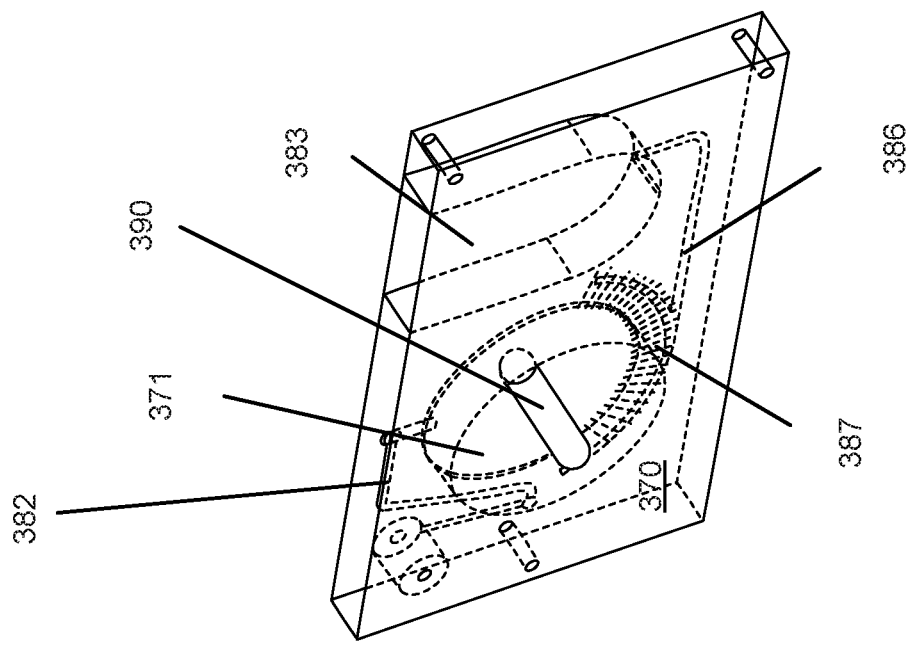
FIG. 3B is an illustration of a mixing assembly, in accordance with an embodiment of the disclosed subject matter.
Figure 3A:
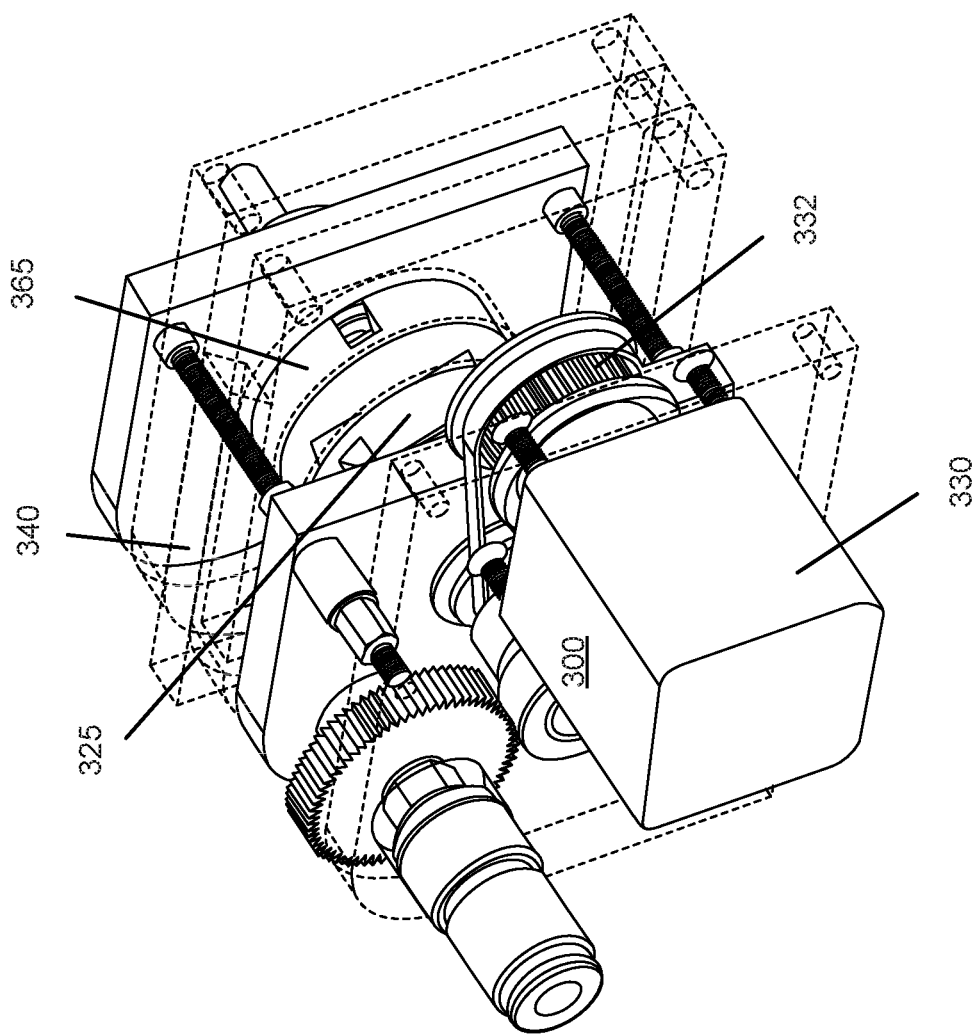
FIG. 3A is an illustration of a magnetic mixing apparatus, in accordance with an embodiment of the disclosed subject matter.

In certain embodiments, rotation of the driving magnet system can be achieved by operably coupling the driving magnet system to a driving magnet spindle 121 and operably coupling the driving magnet spindle to a drive motor (shown in FIG. 3A). The driving magnet rotational axis preferably is parallel to the driving magnet spindle. More preferably, the driving magnet rotational axis is substantially collinear with the driving magnet spindle. In an alternative embodiment discussed in greater detail with regard to FIGS. 3A-5, the one or more driving magnets are mounted in a driving magnet holder (shown in FIG. 3A) and the driving magnet holder is configured to rotate about the driving magnet rotational axis. In such embodiments, this rotation of the driving magnet holder can be achieved by operably coupling the driving magnet holder to the driving magnet spindle and operably coupling the driving magnet spindle to the drive motor. In alternative embodiments, the magnetic mixing apparatus may not include the driving magnet spindle. For example, in embodiments in which the driving magnet holder is circular in shape, rotation of the driving magnet system can be generated from a peripheral drive.

In further embodiments, the driven magnet system is configured to rotate about a driven magnet rotational axis 160. As shown in FIG. 1, the driven magnet system comprises a single driven magnet having a driven magnet rotational axis parallel to the driven magnet magnetic axis. In such single driven magnet systems, preferably, the driven magnet rotational axis is substantially collinear with the driven magnet magnetic axis. In a preferred embodiment, the driven magnet system is symmetric with respect to the driven magnet rotational axis.

Similar to the driving magnet system, the driven magnet system can be operably coupled to a driven magnet spindle 161. Usually, the driven magnet rotational axis is parallel to the driven magnet spindle. In further embodiments, the driven magnet rotational axis can be substantially collinear with the driven magnet spindle. In an alternative embodiment discussed in greater detail with regard to FIGS. 3A-5, the one or more driven magnets are mounted in a driven magnet holder (shown in FIG. 3A) and the driven magnet holder is configured to rotate about the driven magnet rotational axis. In such embodiments, the driving magnet holder can be operably coupled to the driven magnet spindle.

In certain embodiments, the driven magnet rotational axis is parallel to the driving magnet rotational axis. The driven magnet rotational axis can also be substantially collinear with the driving magnet rotational axis. Collinearity of the driven magnet rotational axis and the driving magnet rotational axis is a preferred embodiment because it enhances the strength of the attractive magnetic coupling between the driving magnet system and the driven magnet system, by maximizing alignment of the driving magnet(s) and driven magnet(s) as they rotate about their respective axes.

As a result of the attractive magnetic coupling between the driving magnet system and the driven magnet system, rotation of the driving magnet(s) about the driving magnet rotational axis induces rotation of the driven magnet(s) about the driven magnet rotational axis. Specifically, when the driving magnet system rotates about the driving magnet rotational axis, the driven magnet system rotates about the driven magnet rotational axis such that the strength of the attractive magnetic coupling between the one or more driving magnets and the one or more driven magnets is maximized. As briefly discussed above, to maximize the strength of the attractive magnetic coupling between the one or more driving magnets and the one or more driven magnets, the one or more driven magnets rotate about the driven magnet rotational axis such that opposing poles of the magnetic axis of each of the one or more driving magnets and the magnetic axis of the corresponding one or more driven magnets are located in proximity to one another. Specifically, to maximize the strength of the attractive magnetic coupling between the driving magnet and the driven magnet, the driven magnet rotates about the driven magnet rotational axis such that the driven magnet magnetic axis is as close to collinear with the corresponding driving magnet magnetic axis as possible.

The stir bar is also capable of rotating about the stir bar rotational axis. As a result of the magnetic coupling between the stir bar, the driving magnet system, and the driven magnet system, rotation of the one or more driving magnets about the driving magnet rotational axis and rotation of the one or more driven magnets about the driven magnet rotational axis induces rotation of the stir bar about the stir bar rotational axis.

The rotational axis about which the stir bar rotates is aligned with respect to the stir bar based on the alignment of a driving magnet magnetic axis and driven magnet magnetic axis. As described above, the stir bar is aligned within the mixing chamber such that the greatest magnetic flux possible travels through the stir bar. To maximize the magnetic flux traveling through the stir bar, the largest dimension of the stir bar permissible by the bounding surfaces is parallel to the driving magnet magnetic axis and the to the driven magnet magnetic axis. To maintain this greatest magnetic flux traveling through the stir bar when rotation of the stir bar is induced by rotation of the driving magnet system and the driven magnet system, the stir bar rotates about the stir bar rotational axis such that the largest volume of the stir bar remains within the strongest portions of the magnetic field formed between the one or more driving magnets and the one or more driven magnets as possible. In a preferred embodiment, the stir bar rotational axis is substantially collinear with the magnetic axis of the driving magnetic system and the magnetic axis of the driving magnetic system.

In an ultimately preferred embodiment, the driving magnet magnetic axis, the driven magnet magnetic axis, the driving magnet rotational axis, the driven magnet rotational axis, and the stir bar rotational axis are all substantially collinear with one another. This is a preferred embodiment because it enables the stir bar to be substantially centered or "balanced" within the mixing chamber such that the stir bar minimally contacts the bounding surface of the mixing chamber. Specifically, in a preferred embodiment, the stir bar is positioned within the mixing chamber such that a plane of rotation of the stir bar is equidistant from the driving magnet system and the driven magnet system. The plane of rotation of the stir bar is perpendicular to the stir bar rotational axis. In a further embodiment, the plane of rotation of the stir bar is parallel to the largest dimension of the stir bar. As a result of this equidistance, in a preferred embodiment, the stir bar minimally contacts the bounding surface of the mixing chamber. Decreasing the amount of contact between the stir bar and the bounding surface of the mixing chamber is discussed in greater detail below.

In certain embodiments of the magnetic mixing apparatus, an acoustic mechanism for detecting magnetic decoupling of the stir bar from the driving magnet system and/or the driven magnet system during mixing can be optionally included in the magnetic mixing apparatus. As the angular velocity of the stir bar increases as the stir bar rotates, an amplitude of vibrations produced by the rotating stir bar increases. If the stir bar decouples from the driving magnet system and the driven magnet system, the amplitude of the vibrations produced by the rotating stir bar suddenly decreases, often immediately following several loud knocks.

In some embodiments, the mechanism used to detect decoupling of the stir bar can be a microphone (not shown). In a preferred embodiment, the microphone is directional, and focused on the mixing assembly. However, in alternative embodiments, the microphone can be non-directional and simply placed in proximity to the mixing assembly.

In certain embodiments, the audio output from the stir bar can be bandpass filtered, such that only certain relevant frequencies are measured. Additionally, in some embodiments, the exact frequency and amplitude associated with a decoupling event can be experimentally determined for a given magnetic mixing assembly, and used by the microphone to detect decoupling of the stir bar.

In alternative embodiments, instead of using a microphone, the mechanism used to detect decoupling of the stir bar can be an accelerometer (not shown) that is attached to the mixing assembly. The accelerometer can be used to detect the sudden decrease in amplitude that occurs when the stir bar decouples.

FIG. 2 is a profile view of a schematic diagram of a magnetic mixing apparatus 200, in accordance with an embodiment. The magnetic mixing apparatus includes a driving magnet system 210 and a driven magnet system 250. In the embodiment depicted in FIG. 2, the driving magnet system comprises a first driving magnet 211 and a second driving magnet 216 separated by a distance that transects the driving magnet rotational axis 220, and the driven magnet system comprises a first driven magnet 251 and a second driven magnet 256 separated by a distance that transects the driven magnet rotational axis 260.

The first driving magnet, the second driving magnet, the first driven magnet, and the second driven magnet each have a magnetic axis. Specifically, the first driving magnet has a first driving magnet magnetic axis 213, the second driving magnet has a second driving magnet magnetic axis 218, the first driven magnet has a first driven magnet magnetic axis 253, and the second driven magnet has a second driven magnet magnetic axis 258. In a preferred embodiment, the first driving magnet magnetic axis and the second driving magnet magnetic axis are parallel to one another, and the first driven magnet magnetic axis and the second driven magnet magnetic axis are parallel to one another. In an even further preferred embodiment, the first driving magnet magnetic axis, the second driving magnet magnetic axis, the first driven magnet magnetic axis, and the second driven magnet magnetic axis are parallel to one another. In an ultimately preferred embodiment, the first driving magnet magnetic axis and the first driven magnet magnetic axis are substantially collinear with one another and the second driving magnet magnetic axis and the second driven magnet magnetic axis are substantially collinear with one another. In a further preferred embodiment, the poles of the first driving magnet are arranged with respect to the first driving magnet magnetic axis in the same arrangement as the poles of the second driving magnet with respect to the second driving magnet magnetic axis. Similarly, in a preferred embodiment, the poles of the first driven magnet are arranged with respect to the first driven magnet magnetic axis in the same arrangement as the poles of the second driven magnet with respect to the second driven magnet magnetic axis. In a further preferred embodiment, a magnet strength of the first driving magnet equals a magnet strength of the second driving magnet, and a magnet strength of the first driven magnet equals a magnet strength of the second driven magnet. In an even further preferred embodiment, magnet strengths of the first driving magnet, the second driving magnet, the first driven magnet, and the second driven magnet are all the same.

When separated by a distance, the first driving magnet and the second driving magnet can comprise any shape and/or size. Similarly, when separated by a distance, the first driven magnet and the second driven magnet can comprise any shape and/or size. In a preferred embodiment, a shape of the first driving magnet is the same as a shape of the second driving magnet, and a shape of the first driven magnet is the same as a shape of the second driven magnet. In a further preferred embodiment, a shape of the first driving magnet, a shape of the second driving magnet, a shape of the first driven magnet, and a shape of the second driven magnet are all the same. For example, in the embodiment depicted in FIG. 2, the first driving magnet, the second driving magnet, the first driven magnet, and the second driven magnet each comprise a cube. In an additional preferred embodiment, dimensions of the first driving magnet are the same as dimensions of the second driving magnet, and dimensions of the first driven magnet are the same as dimensions of the second driven magnet. In a further preferred embodiment, dimensions of the first driving magnet, the second driving magnet, the first driven magnet, and the second driven magnet are all the same.

In a preferred embodiment, the first driving magnet is located approximately an equal distance from the driving magnet rotational axis as the second driving magnet. Similarly, in a preferred embodiment, the first driven magnet is located approximately an equal distance from the driven magnet rotational axis as the second driven magnet. In a further preferred embodiment, the first driving magnet, the second driving magnet, the first driven magnet, and the second driven magnet are all located an equivalent distance from their respective rotational axes. This is a preferred embodiment because it enables the magnets to generate symmetric magnetic fields with respect to their rotational axes. In an additional preferred embodiment, the first driving magnet is located approximately an equal distance from a mixing chamber 271 as the second driving magnet. Similarly, in a preferred embodiment, the first driven magnet is located approximately an equal distance from the mixing chamber as the second driven magnet. In a further preferred embodiment, the first driving magnet, the second driving magnet, the first driven magnet, and the second driven magnet are all located an equivalent distance from the mixing chamber. This is a preferred embodiment because it enables the magnets to generate symmetric magnetic fields with respect to the mixing chamber.

In embodiments of the driving magnet system and the driven magnet system in which the driving magnet system comprises first driving magnet and the second driving magnet and the driven magnet system comprises a first driven magnet and a second driven magnet separated by a distance, the largest dimension of the driving magnet system is the distance from the outside edge of the first driving magnet to the outside edge of the second driving magnet, including the any intervening spacer, and a largest dimension of the driven magnet system comprises the distance from the outside edge of the first driven magnet to the outside edges of the second driven magnet, including any intervening spacer. As described with regard to FIG. 1 or FIG. 2, the largest dimension of the driving magnet system typically is in a plane perpendicular to the rotational axis of the driving magnetic system. Similarly, the largest dimension of the driven magnet system typically is in a plane perpendicular to the rotational axis of the driven magnet system. A shortest dimension of the driving magnet system is orthogonal to the largest dimension of the driving magnet system and a shortest dimension of the driven magnet system is orthogonal to the largest dimension of the driven magnet system. In some embodiments, the driving magnet system comprises a spacer that bridges the distance between the first driving magnet and the second driving magnet, and connects the first driving magnet and the second driving magnet. In such embodiments, the spacer transects the driving magnet rotational axis. In further embodiments, the driven magnet system comprises a spacer that bridges the distance between the first driven magnet and the second driven magnet, and connects the first driven magnet and the second driven magnet. In such embodiments, the spacer transects the driven magnet rotational axis. In systems comprising three or more magnets, one of skill in the art will appreciate that the geometry of the spacer can be adapted to be capable of bridging more than two points and intercept the driving magnet spindle or driven magnet spindle.

Figure 4:
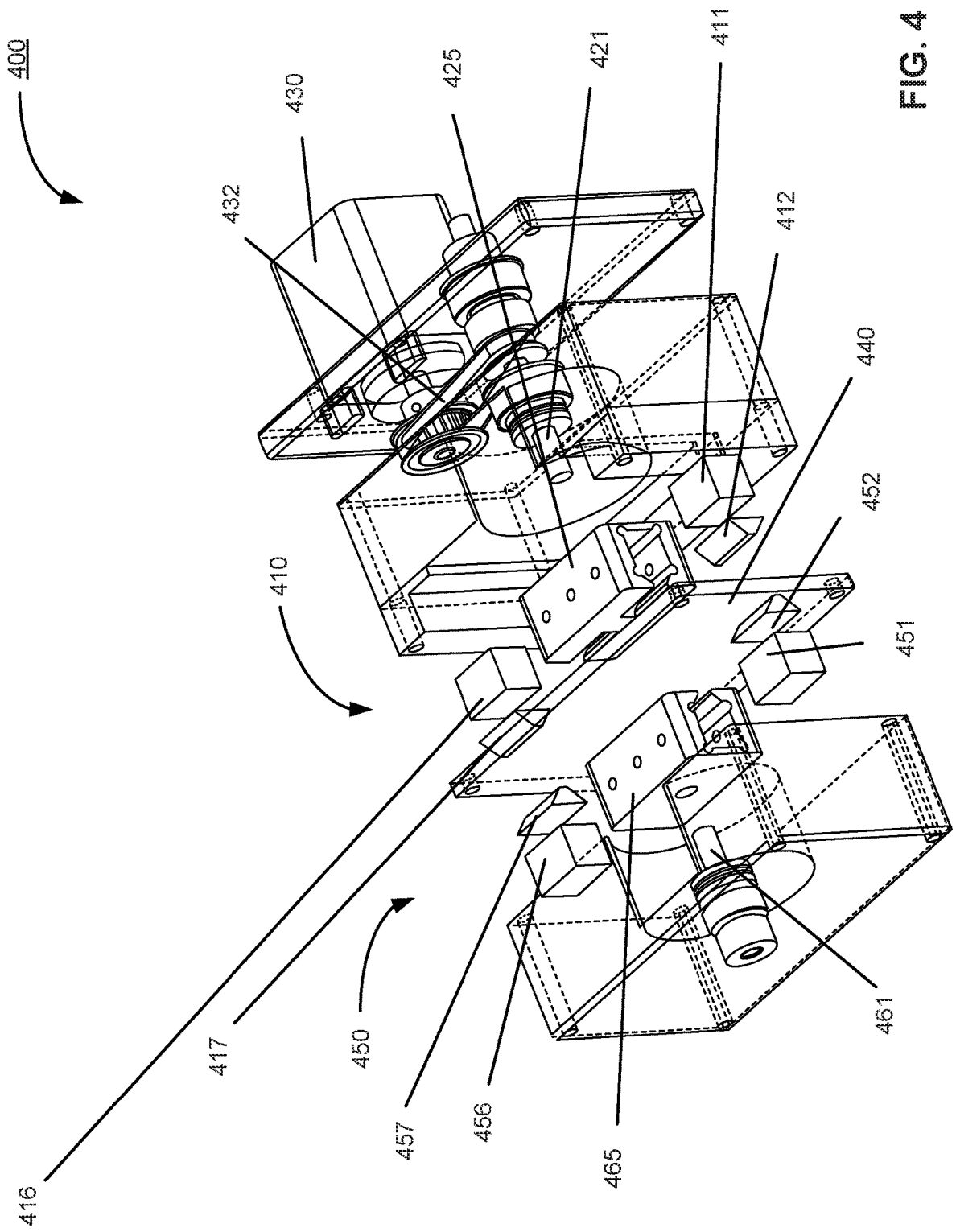
FIG. 4 is an illustration of an exploded view of a magnetic mixing apparatus, in accordance with an embodiment.

The spacer that connects the first driving magnet and the second driving magnet and/or the first driven magnet and the second driven magnet can take any form. For example, as shown in FIG. 4, the first driving magnet and the second driving magnet can be mounted and held in a driving magnet holder 425, and the first driven magnet and the second driven magnet can be mounted and held in a driven magnet holder 465.

In some embodiments, a driving magnet spindle 221 is positioned between the first driving magnet and the second driving magnet and/or a driven magnet spindle 261 is positioned between the first driven magnet and the second driven magnet. In embodiments in which a spacer connects the first driving magnet to the second driving magnet and the first driven magnet to the second driven magnet (as illustrated in FIG. 2), the driving magnet spindle and the driven magnet spindle can be connected to the respective spacer.

Devices

FIG. 3A is an illustration of one embodiment of a magnetic mixing apparatus 300, in accordance with the present disclosure. As shown in FIG. 3A, the magnetic mixing apparatus includes a driving magnet holder 325, a driven magnet holder 365, and a gap located between the driving magnet holder and the driven magnet holder. In some embodiments, the driving magnet system (in some embodiments the single, first driving magnet of FIG. 1 and in alternative embodiments more than one driving magnet, e.g., the first driving magnet and the second driving magnet of FIG. 2) is mounted within the driving magnet holder and the driven magnet system (in some embodiments the single, first driven magnet of FIG. 1 and in alternative embodiments more than one driven magnet, e.g., the first driven magnet and the second driven magnet of FIG. 2) is mounted within the driven magnet holder. The driving magnet holder holds the driving magnet system in a stationary position and the driven magnet holder holds the driven magnet system in a stationary position in accordance with the embodiments discussed with regard to FIGS. 1 and 2. In a preferred embodiment, the driving magnet holder comprises the same specifications (e.g., shape, size, material composition, and/or weight) as the driven magnet holder. In a preferred embodiment, the driving magnet holder and the driven magnet holder are aligned with one another across the gap which is configured to accommodate a mixing chamber.

As also discussed above with regard to FIGS. 1 and 2, in some embodiments, the driving magnet system is configured to rotate around the driving magnet rotational axis. In embodiments in which the driving magnet system is mounted within the driving magnet holder, the driving magnet holder can be configured to rotate around the driving magnet rotational axis. For example, the driving magnet holder can be operably coupled to a drive motor 330, 430 that is capable of driving rotation of the driving magnet holder about the driving magnet rotational axis. In further embodiments, the driving magnet holder can be mechanically coupled to the drive motor. The drive motor can be in line with and directly drive rotation of the driving magnet holder. Alternatively, the drive motor can be indirectly, but operably, coupled to the driving magnet spindle. In such embodiments, the driving magnet spindle can be operably and/or mechanically coupled to a drive belt 332, 432, which in turn can be operably and/or mechanically coupled to the drive motor that is capable of driving rotation of the driving magnet holder about the driving magnet rotational axis. When coupled to the drive motor, the drive belt is capable of rotating the driving magnet spindle such that the driving magnet holder that is operably coupled to the driving magnet spindle, rotates.

In alternative embodiments, the driving magnet system is not mounted within the driving magnet holder. Instead, the driving magnet system itself can be operably and/or mechanically coupled to the drive motor. This operative and/or mechanical coupling between the driving magnet system and the drive motor can be via the drive belt and/or the driving magnet spindle as described above.

As also discussed above with regard to FIGS. 1 and 2, the driven magnet system is configured to rotate around the driven magnet rotational axis. In embodiments in which the driven magnet system is mounted within the driven magnet holder, the driven magnet holder can be configured to rotate around the driven magnet rotational axis. In some embodiments, the driven magnet holder can be operably coupled to the driven magnet spindle. In such embodiments, the driven magnet spindle can be substantially collinear with the driven magnet rotational axis.

In certain embodiments, a mixing assembly holder 340, 440 is disposed within the gap between the driving magnet holder and the driven magnet holder. A mixing assembly that is configured to be held in a stationary position within the mixing assembly holder is discussed in further detail with regard to FIG. 3B. In alternative embodiments, there is no mixing assembly holder and the mixing assembly is itself disposed directly in the gap between the driving magnet holder and the driven magnet holder.

FIG. 3B is an illustration of a mixing assembly 370, in accordance with an embodiment of the disclosed subject matter. As shown in FIG. 3B, the mixing assembly comprises a mixing chamber 371, a stir bar 390, a sample loading well 383, a sample transfer channel 386, an air channel 382, and bead filter channels 387. In alternative embodiments of the mixing assembly, such as those discussed with regard to FIGS. 8A-D, the mixing assembly can comprise additional fluid channels and/or air channels. In certain embodiments, the mixing assembly is configured to be disposable. In alternative embodiments, the mixing assembly is configured to be sanitizable, e.g., with bleach and/or alternative cleaning material, to permit multiple uses.

The sample loading well is configured to receive a fluid sample from a sample inlet (illustrated in FIG. 8A) and contain the fluid sample prior to transfer of the fluid sample to the mixing chamber. In some embodiments, the mixing chamber holds a first liquid, such as a lysis buffer, while the sample chamber contains the fluid sample. In some embodiments the fluid sample comprises one or more cells. The sample transfer channel is configured to transport the fluid sample from the sample loading well into the mixing chamber. An air outlet is configured to transfer air between an air port and the air channel. The air channel transfers air between the air outlet and the mixing chamber. As discussed in greater detail with regard to FIGS. 8A-D, the pressure of the air within the air channel controls the operation of the mixing assembly, and specifically controls the entry and exit of fluids to and from the mixing chamber.

In some embodiments, the mixing chamber further comprises beads (shown in FIGS. 8A-D). In embodiments in which the fluid sample transferred to the mixing chamber comprises one or more cells, mixing the fluid sample with the beads promotes lysis of the one or more cells. Following mixing of the fluid sample with the beads, the fluid sample is removed from the mixing chamber. In a preferred embodiment, the beads are separated from the fluid sample in conjunction with the sample being removed from the mixing chamber. To separate the beads from the fluid sample, in some embodiments, bead filter channels are appended to the mixing chamber. The bead filter channels are located along an edge of the mixing chamber and are configured to retain the beads in the mixing chamber while allowing the fluid sample to exit. Specifically, in a preferred implementation, a cross sectional area of each bead filter channel comprises a first dimension such that the beads are too large to enter the bead filter channels, and a second dimension such that the beads are unable to block fluid flow. In this way use of the bead filter channels enables fluid to be drawn from the mixing chamber without beads.

FIG. 4 is an illustration of an exploded view of a magnetic mixing apparatus 400, in accordance with an embodiment. In the embodiment depicted in FIG. 4, a driving magnet system 410 comprises a first driving magnet 411 and a second driving magnet 416 separated by a distance, and a driven magnet system 450 comprises a first driven magnet 451 and a second driven magnet 456 separated by a distance as shown in FIG. 2.

As discussed above with regard to FIG. 1, in areas in which the magnetic fields generated by the driving magnet system and the driven magnet system overlap, the overall magnetic field produced as a result of this overlap comprises a magnetic field with parallel magnetic field lines. Specifically, in areas in which the magnetic fields generated by the driving magnet system and the driven magnet system overlap, the magnetic field produced consists of parallel magnetic field lines traveling from the driving magnet system to the driven magnet system, and from the driven magnet system to the driving magnet system.

Figure 5:
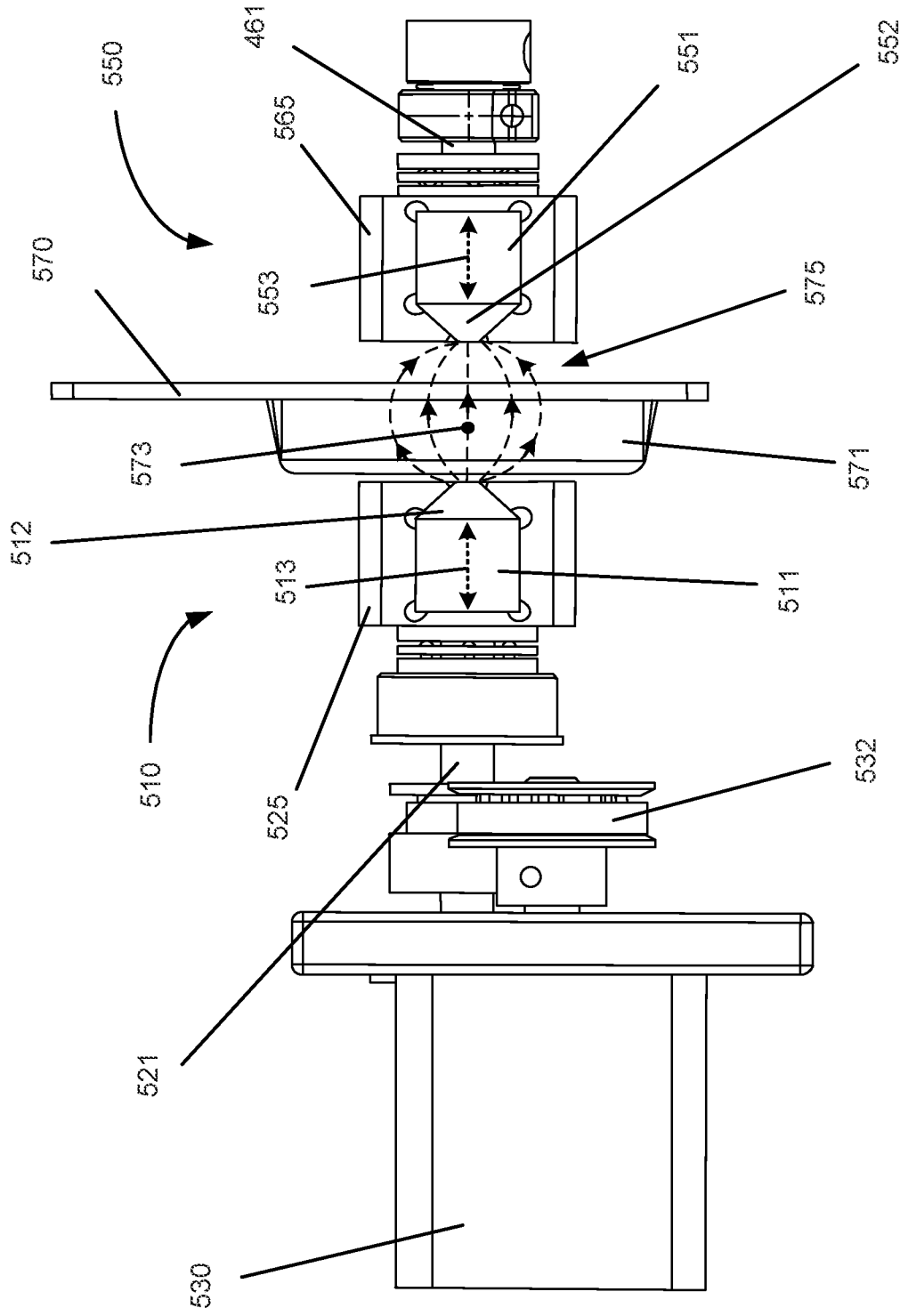
FIG. 5 is an illustration of a profile view of a magnetic mixing apparatus, in accordance with an embodiment.

To increase the torque of the stir bar, certain embodiments of the magnetic mixing apparatus can comprise one or more field focusers. Preferably, the field focusers are coupled to at least one of the one or more driving magnets or the one or more driven magnets, and are positioned to focus magnetic fields generated by the driving magnet system and the driven magnet system towards a narrow radial segment along a largest dimension of the driving and driven magnetic systems. Field focusers can be coupled to the one or more magnets of the driving magnet system and/or the driven magnet system, and steepen the magnetic field gradient across the gap. The field focusers concentrate the magnetic fields generated by the driving magnet system and the driven magnet system into a smaller cross-sectional area, thereby increasing the magnetic flux passing through the stir bar. By steepening the magnetic field gradients, the field focusers increase the potential torque on the stir bar during rotation of the stir bar. Magnetic field lines of the driving magnet system and the driven magnet system that have been transformed by field focusers are depicted in FIG. 5. In the absence of a field focuser, the approximately equivalent magnet strength would be distributed over the larger area of the face of the magnet (e.g. 511).

As shown in FIG. 4, the driving magnet system and the driven magnet system can each be coupled to a field focuser. For instance, in the embodiment of the magnetic mixing apparatus depicted in FIG. 4, the first driving magnet, the second driving magnet, the first driven magnet, and the second driven magnet are each coupled to a field focuser. Specifically, the first driving magnet is coupled to a first driving magnet field focuser 412, the second driving magnet is coupled to a second driving magnet field focuser 417, the first driven magnet is coupled to a first driven magnet field focuser 452, and the second driven magnet is coupled to a second driven magnet field focuser 457. In alternative embodiments in which the driving magnet system and the driven magnet system comprise monolithic magnets (as shown in FIG. 1), a single field focuser can be coupled to each of the single driving magnet and the single driven magnet.

In certain embodiments, the field focusers are comprised of iron. Iron is permeable to magnetic fields, meaning that magnetic fields generated by the driving magnet system and/or the driven magnet system can pass through iron field focusers that are coupled to the driving magnet system and/or the driven magnet system. In further embodiments, the field focusers, are triangular-prism shaped. In embodiments in which the field focusers are coupled to the driving magnet system and the driven magnet system, the field focusers are positioned to focus magnetic fields that are generated by the driving magnet system and the driven magnet system towards the center of the mixing chamber. These magnetic field gradients constrain the stir bar to the center of the mixing chamber. The use of field focusers in the magnetic mixing apparatus is optional. In alternative embodiments, the magnetic mixing apparatus does not comprise field focusers.

FIG. 5 is an illustration of a profile view of a magnetic mixing apparatus 500, in accordance with an embodiment. Specifically, FIG. 5 includes a drive motor 530, a drive belt 532, a driving magnet spindle 521, a driving magnet holder 525, a mixing assembly 570, a driven magnet holder 565, and a driven magnet spindle 561 arranged to mix a sample contained within a mixing chamber 571 of the mixing assembly. As shown in FIG. 5, the drive motor is operably/mechanically coupled to the drive belt, which is operably/mechanically coupled to the driving magnet spindle, which is in turn operably coupled to the driving magnet holder. The driving magnet holder contains a driving magnet system 510 (in some embodiments, a first driving magnet 511 and a second driving magnet (not shown)). As discussed above, the driving magnet holder is positioned in proximity to a first face of the mixing assembly such that the driving magnet holder is aligned with the mixing chamber. The driven magnet holder is positioned in proximity to a second face of the mixing assembly that is opposite the first face, such that the driven magnet holder is also aligned within the mixing chamber, and such that the mixing chamber is located between the driving magnet holder and the driven magnet holder. The driven magnet holder contains a driven magnet system 550 (in some embodiments, the first driven magnet 551 and the second driven magnet (not shown)). Finally, the driven magnet holder is operably coupled to the driven magnet spindle.

As discussed above with regard to FIG. 4, in certain embodiments such as the embodiment depicted in FIG. 5, a first driving magnet field focuser 512 can be coupled to the first driving magnet and/or a first driven magnet field focuser 552 can be coupled to the first driven magnet. The first driving magnet field focuser and the first driven magnet field focuser transform the magnetic field lines produced by the first driving magnet and the first driven magnet to produce magnetic field lines 575 shown in FIG. 5. As discussed above, the magnetic field lines comprise a gradient pattern, with a lowest magnetic field strength near the exterior edges of the magnet, and a greatest magnetic field strength near a center 573 of the magnet.

Turning to the alignment of the driving magnet holder and the driven magnet holder, in some embodiments, the driving magnet holder and the driven magnet holder are located approximately an equal distance from the center of the mixing chamber. For example, the driving magnet holder and the driven magnet holder can each be located a distance of 7 mm from the center of the mixing chamber. In further embodiments, the driving magnet system and the driven magnet system can be located an equal distance from the center of the mixing chamber. For example, the driving magnet system and the driven magnet system can each be located a distance of 7 mm from the center of the mixing chamber. In an even further embodiment, the first driving magnet field focuser and the first driven magnet field focuser can be located an equal distance from the center of the mixing chamber. For example, the first driving magnet field focuser and the first driven magnet field focuser can each be located a distance of 7 mm from the center of the mixing chamber.

Figure 6:
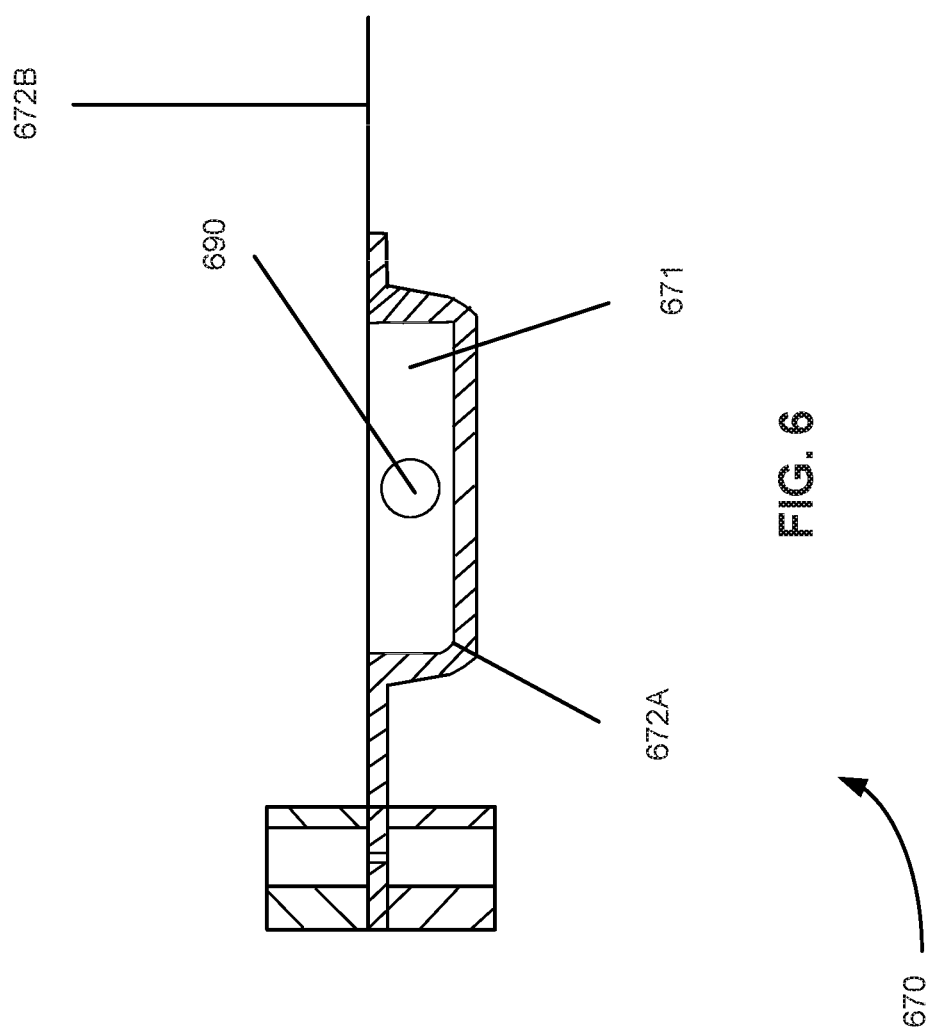
FIG. 6 is an illustration of a cross section of a profile view of a mixing assembly, in accordance with an embodiment.
Figure 7:
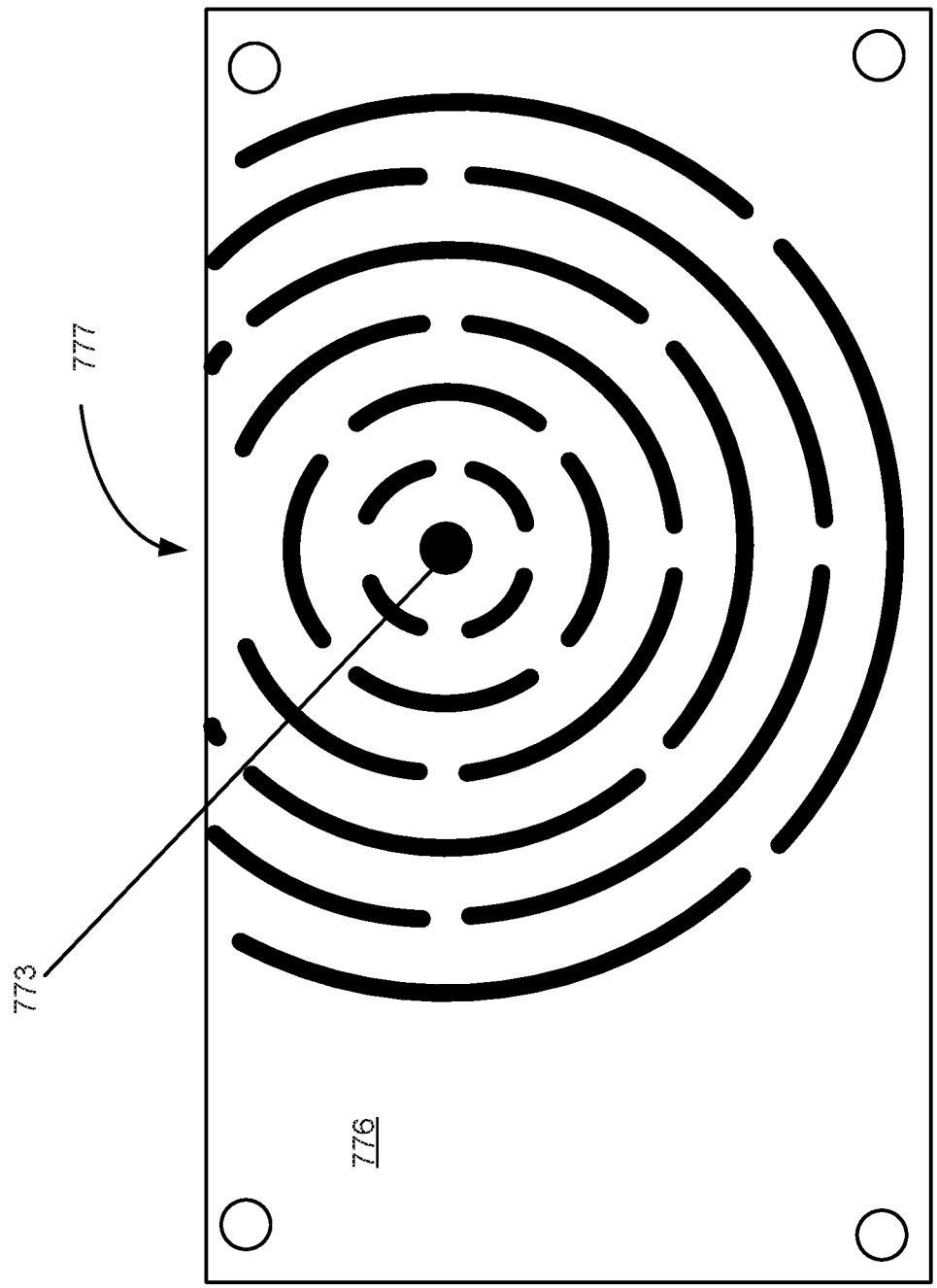
FIG. 7 illustrates a supportive plate, in accordance with an embodiment.

FIG. 6 is an illustration of a cross section of a profile view of a mixing assembly 670, in accordance with an embodiment. Specifically, FIG. 6 depicts a stir bar 690 located within a mixing chamber 671. Note that bounding surfaces 672A and 672B of the mixing chamber need not be of uniform thickness on all faces of the mixing chamber. In some implementations, it is desirable to heat or cool the contents of the mixing chamber. Therefore, in certain embodiments, one wall of the mixing chamber (for example a bounding surface 672B) is relatively thin and thermally conductive. In embodiments in which a bounding surface of the mixing chamber is thin, a supportive plate (not shown) can be positioned adjacent to the thin bounding surface to support the spinning stir bar and/or the pressurized filling of the mixing chamber (discussed with regard to FIGS. 8A-D). An embodiment of the supportive plate is depicted in FIG. 7 and discussed in greater detail below.

As noted above with regard to FIG. 1, in a preferred embodiment, the stir bar minimally contacts the bounding surface of the mixing chamber. In certain embodiments, to avoid contact between the stir bar and the bounding surface, the dimensions of the mixing chamber and stir bar are proportioned such that the stir bar seldom contacts the bounding surface of the mixing chamber.

In further embodiments, to further avoid contact between the stir bar and the bounding surface of the mixing chamber, a largest dimension of the mixing chamber will be less than largest dimension 694 of the stir bar. For instance, in certain embodiments, the largest dimension of the mixing chamber can be 1 mm-10 mm greater than a largest dimension of the stir bar. For example, in certain embodiments, the largest dimension of the mixing chamber volume can comprise between 1 mm-200 mm. In a preferred embodiment, the largest dimension of the mixing chamber volume is selected from the group comprising about 2-100 mm, about 10-80 mm, and about 20-30 mm. In further embodiments, the largest dimension of the stir bar is between 0.5 mm-180 mm. In a preferred embodiment, the largest dimension of the stir bar is selected from the group comprising about 1-100 mm, about 3-50 mm, and about 5-30 mm.

In some embodiments, the stir bar does not contact the bounding surface of the mixing chamber. In alternative embodiments, the stir bar can contact the bounding surface of the mixing chamber, but more infrequently than would if the driving magnet system were present, but the driven magnet system were absent.

In certain embodiments, the mixing chamber volume can comprise between 0.1 mL-100 mL. In a preferred embodiment, the mixing chamber volume is selected from the group comprising about 1-20 mL, about 2-10 mL, and about 3-6 mL. In a further embodiment, the stir bar volume can comprise between 50 uL-10 mL. In a preferred embodiment, the stir bar volume is selected from the group comprising less than 1 mL, about 0.1-0.8 mL, and about 0.3-0.5 mL.

FIG. 7 illustrates a supportive plate 776, in accordance with an embodiment. As discussed above with regard to FIG. 6, in certain embodiments, the supportive plate may be located adjacent to one or more thin bounding surfaces of a mixing chamber to support spinning of a stir bar within the mixing chamber and/or pressurization of the mixing chamber. The supportive plate is located within the gap between the driving magnet system and driven magnet system.

To enable conduction of heat to and from the mixing chamber, the supportive plate can comprise a thermoconductive material, which can be heated and/or cooled in order to heat and/or cool the contents of the mixing chamber. For example, in certain embodiments, the supportive plate can comprise aluminum. In such embodiments in which the supportive plate comprises a conductive material, rotating magnets may induce eddy currents in the supportive plate. Specifically, when one or more magnets rotate around axes that are perpendicular to a conductive plane such as the supportive plate (for example, a driving magnet rotational axis and/or a driven magnet rotational axis), eddy currents can be generated in the conductive plane. These eddy currents have the potential to interact with and create a drag force on the one or more rotating magnets. This drag force can result in a loss of transferred torque between the one or more rotating magnets. For example, drag force on the driving magnet system and/or the driven magnet system can result in a loss of transferred torque from the driving magnet system to the driven magnet system and/or to the stir bar. This loss in transferred torque can cause the one or more rotating magnets to decouple, particularly at high speeds of angular rotation. Specifically, a loss of transferred torque can cause the driven magnet system to decouple from the driving magnet system.

To limit the induction of eddy currents in the supportive plate, and therefore limit the decoupling of the one or more rotating magnets, in some embodiments (such as the embodiment depicted in FIG. 7), the supportive plate can optionally include a plurality of perforations 777. In embodiments of the magnetic mixing apparatus discussed in this disclosure, the driving magnet system and the driven magnet system rotate in a circular pattern. As such, eddy currents that are induced in the supportive plate by the rotating magnet systems are induced radially from a center 773 of the circular pattern. To limit the induction of eddy currents in the supportive plate, the plurality of perforations can be arranged in a concentric pattern around the center of the circular pattern of rotation of the magnet systems. In other words, the plurality of perforations can be arranged concentrically with the mixing chamber and/or with the stir bar contained within the mixing chamber. This concentric arrangement of the plurality of perforations causes the eddy currents induced in the supportive plate to follow a convoluted path along their radial induction pathways. This convoluted pathway limits the formation of the eddy currents in the supportive plate. By limiting the induction of eddy currents in the supportive plate, drag on the rotating magnet systems that is caused by the eddy currents is limited to below a threshold that will interfere with effective coupling of the driving magnet system, driven magnet system and stir bar.

Methods

FIGS. 8A-D illustrate one exemplar mixing method implemented on a mixing assembly 870, according to an embodiment of the invention. As shown in the embodiment depicted in FIGS. 8A-D, the mixing assembly comprises a mixing chamber 871 surrounded by a bounding surface 872. The mixing chamber contains a stir bar 890 and optionally a plurality of beads 874. In order to facilitate loading of a sample, the mixing assembly illustrated in FIGS. 8A-D also includes a sample loading well 883 and a sample transfer channel 886. The sample transfer channel connects the sample loading well and the mixing chamber. It will be understood by those of skill in the art that a separate loading well is not required for proper operation of the method and that the sample may be delivered directly into the mixing chamber by any of a variety of fluidic systems and sample sources. A chamber loading channel 885 permits introduction of reagents, including e.g. a lysis solution or beads into the mixing chamber without interacting with sample in the sample chamber. Pneumatic control of fluid movement is provided by air pressure supplied via an air channel 882.

Figure 8A:
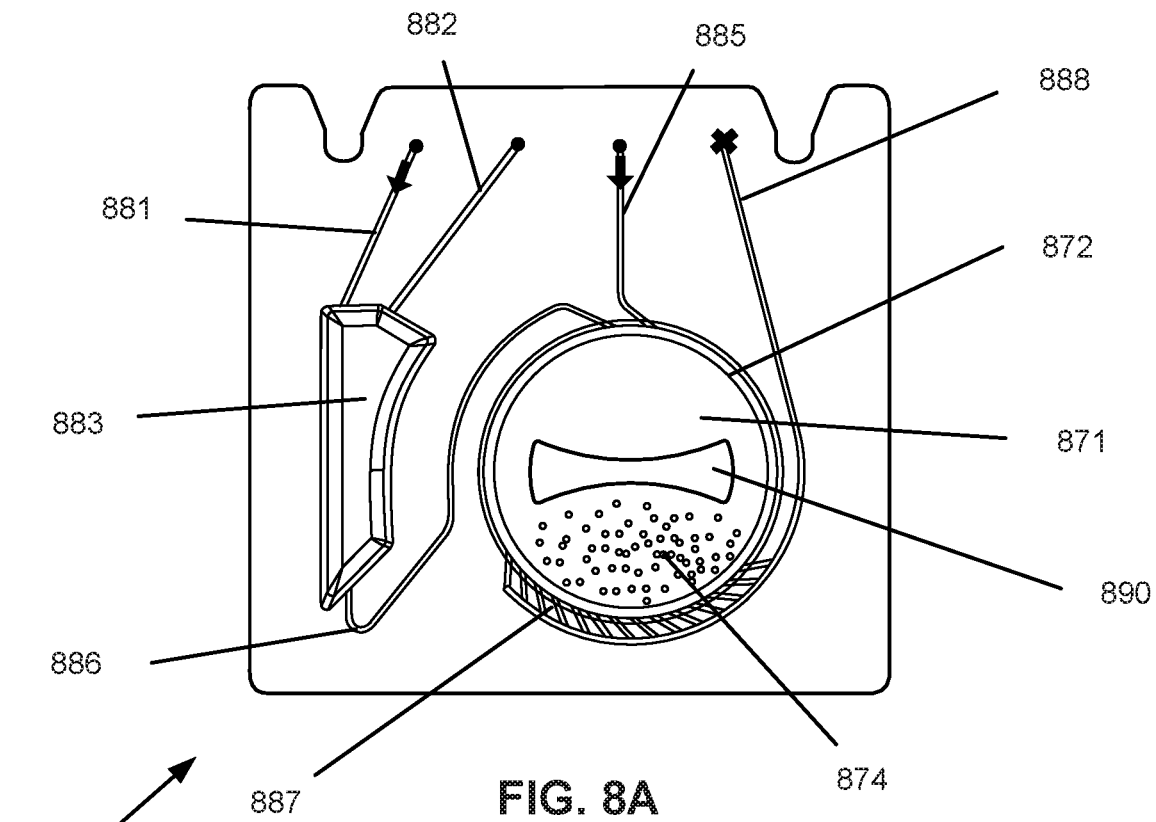
FIG. 8A illustrates a first step of a mixing process performed using a mixing assembly, in accordance with an embodiment.

FIG. 8A illustrates a first step of a mixing process performed using the mixing assembly, in accordance with an embodiment. A sample is loaded into a sample inlet 881 and a lysis buffer is loaded into the chamber loading channel. In some embodiments, the sample comprises one or more cells. In some embodiments, the lysis buffer comprises one or more chemical lysing agents including, but not limited to, hypotonic solutions, and/or solutions containing an organic solvent (such as an alcohol, ether or chloroform), a chelating agent (such as ethylenediaminetetraacetic acid (EDTA)), a surfactant (such as Triton or sodium dodecyl sulfate (SDS)), and/or a chaotropic agent (such as urea or guanidine). In certain embodiments, the lysis buffer can be pre-loaded into the mixing chamber and stored for extended periods within the mixing chamber prior to use of the mixing assembly. The order of addition of the lysis solution, the sample, and the optional beads will not adversely impact the methods described herein.

Figure 8B:
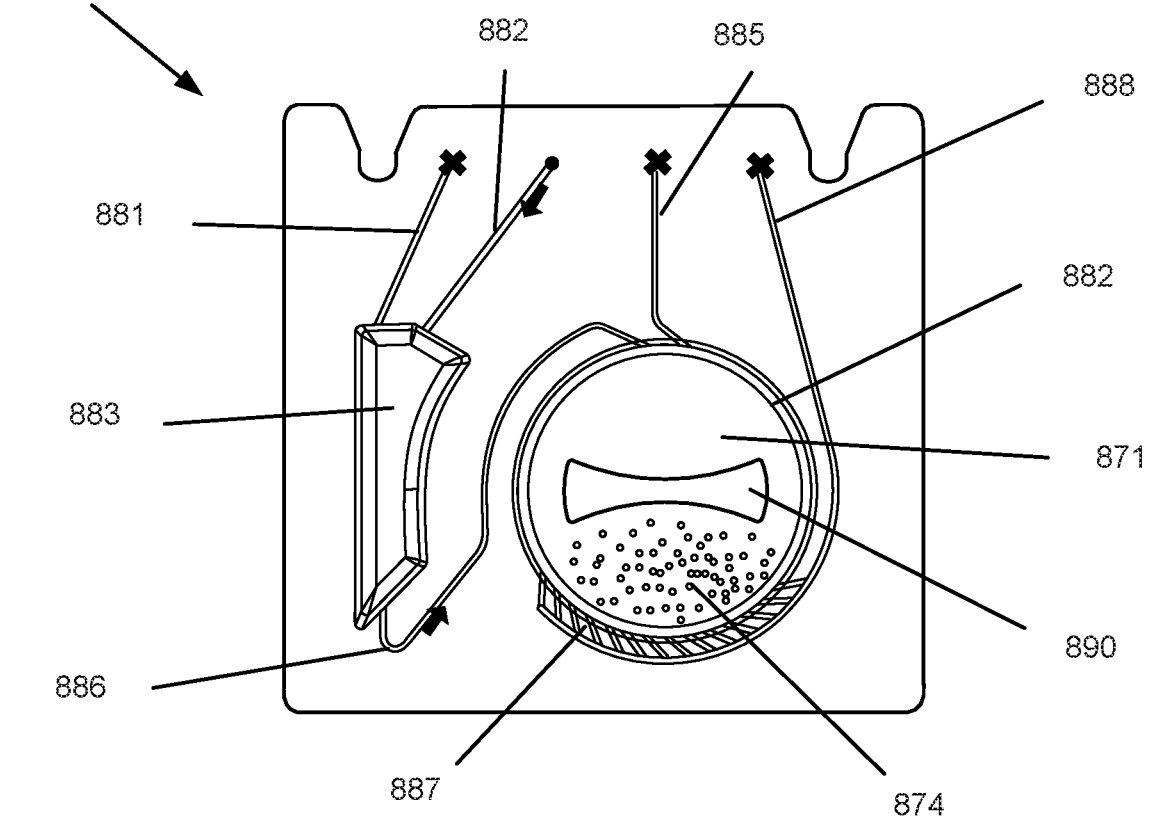
FIG. 8B illustrates a second step of a mixing process performed using a mixing assembly, in accordance with an embodiment.

FIG. 8B illustrates a second step of the mixing process performed using the mixing assembly, in accordance with an embodiment. As shown in FIG. 8B, the sample is located within the sample loading well. The air channel is open, and air is forced through the air channel and into the sample loading well. In some embodiments, the air has an air pressure of 20 psi. The sample inlet is closed so that fluid (including the air from the air channel and/or the sample located in the sample loading well) cannot escape the sample loading well through the sample inlet. As a result, a pressure inside the sample loading well is increased. This increased pressure within the sample loading well causes the sample to be pushed out of the sample loading well, into the sample transfer channel, and finally into the mixing chamber. The chamber loading channel 885 and the sample exit channel 888 are closed such that fluid (such as the lysis buffer and the sample located within the mixing chamber) cannot escape from the mixing chamber.

Figure 8C:
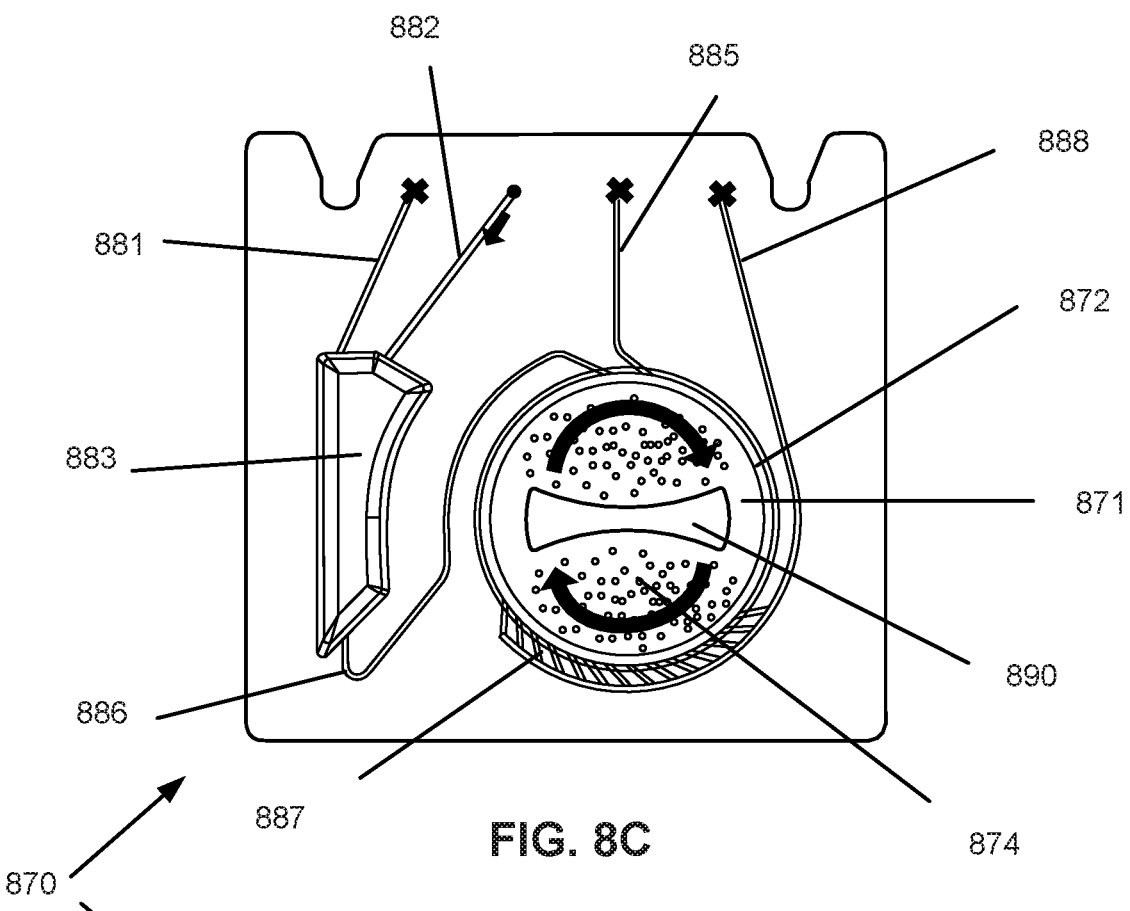
FIG. 8C illustrates a third step of a mixing process performed using a mixing assembly, in accordance with an embodiment.

FIG. 8C illustrates a third step of the mixing process performed using the mixing assembly, in accordance with an embodiment. As shown in FIG. 8C, the sample and the lysis buffer are located within the mixing chamber. The air pressure in the sample loading well is maintained at a constant pressure. The sample inlet, the chamber loading channel, and the sample exit channel remain closed such that such that fluid (such as the lysis buffer and the sample located within the mixing chamber) cannot escape from the mixing chamber. As a result, the sample and the lysis buffer remain enclosed within the mixing chamber.

As shown in FIG. 8C, the stir bar rotates responsive to coupled rotations of the driving and driven magnet systems. In some embodiments, rotation of the stir bar is caused by energizing a drive motor that is operably coupled to a driving magnet system, thereby inducing rotation of the driving magnet system. In turn, the driving magnet system is magnetically coupled to a driven magnet system, and thus rotation of the driving magnet system induces rotation of the driven magnet system. Additionally, the driving magnet system and the driven magnet system are both operably coupled to the stir bar. Thus in some embodiments, rotation of the driving magnet system and rotation of the driven magnet system induces rotation of the stir bar seen in FIG. 8C. This rotation of the stir bar mixes the sample and the lysis buffer located within the mixing chamber. In embodiments, in which the sample comprises one or more cells, mixing of the sample and the lysis buffer promotes lysis of the one or more cells. In further embodiments, the plurality of beads located within the mixing chamber further promote lysis of the one or more cells.

Figure 8D:
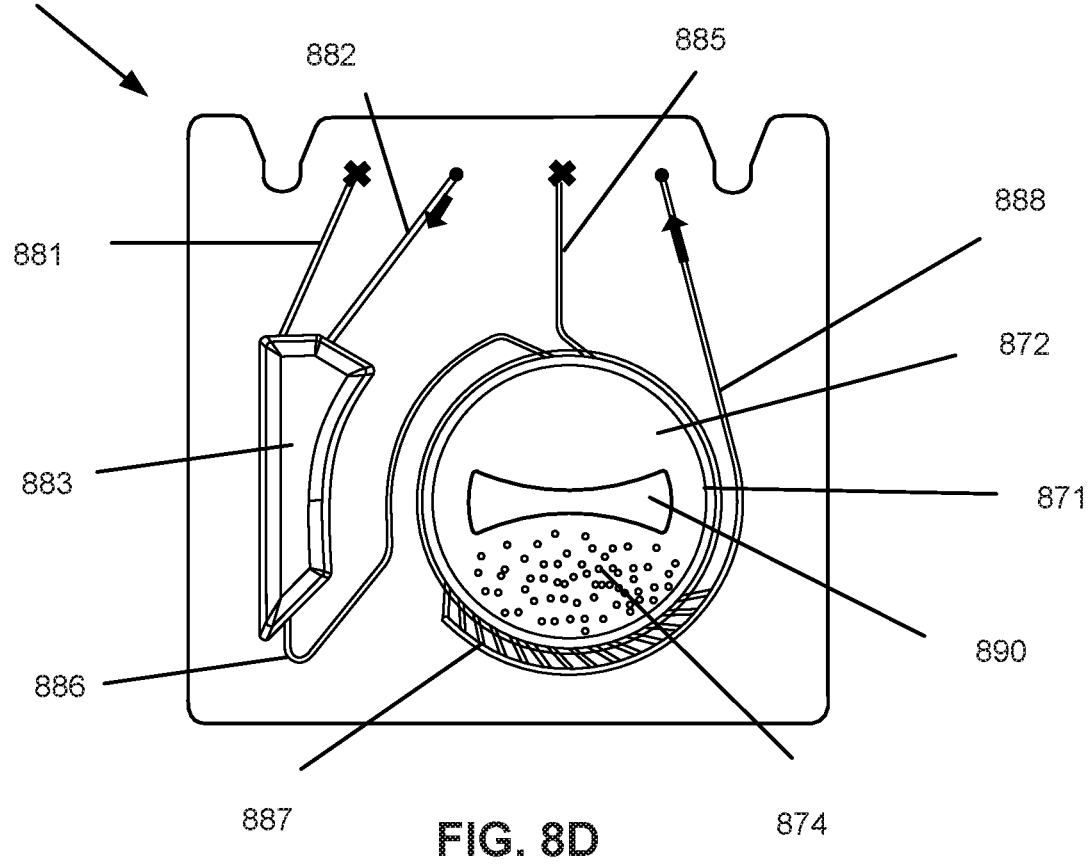
FIG. 8D illustrates a fourth step of a mixing process performed using a mixing assembly, in accordance with an embodiment.

FIG. 8D illustrates a fourth step of the mixing process performed using the mixing assembly, in accordance with an embodiment. As shown in FIG. 8D, rotation of the stir bar has stopped, and the sample and the lysis buffer are located within the mixing chamber. In some embodiments, in FIG. 8D the sample comprises a lysed sample as a result of the mixing shown in FIG. 8C.

As further shown in FIG. 8D, the air channel is open, and pneumatic pressure is applied to the air channel and into the sample loading well. The sample inlet and the chamber loading channel remain closed such that such that fluid (e.g., the mixed lysis buffer and the sample) cannot escape from the mixing chamber via the sample inlet and/or the chamber loading channel. However, the sample exit channel is now open. As a result, of the positive air pressure from the air channel, the lysed sample can travel out of the mixing chamber, through the sample exit channel, and into the environment of the mixing assembly where the lysed sample can be collected.

In some embodiments, the beads are separated from the fluid sample in conjunction with the sample being removed from the mixing chamber. To separate the beads from the fluid sample, bead filter channels 887 located along an edge of the mixing chamber retain the beads in the mixing chamber while allowing the fluid sample to exit the mixing chamber. Specifically, a cross sectional area of each bead filter channel comprises a first dimension such that the beads are too large to enter the bead filter channels, and a second dimension such that the beads are unable to block fluid flow. In this way use of the bead filter channels enables the lysed sample to be removed from the mixing chamber without beads.

Examples

Phosphate buffered saline (PBS) was spiked with titered *Candida albicans* at a concentration of 1000 CFU/ml and supplemented with bovine serum albumin (BSA) to a final concentration of 0.9 mg/ml. A prefilled tube containing 0.7 mL dry volume of 0.1 & 0.5 mm zirconia beads (Zymo Research BashingBead™, catalog no. S6012-50) was added to the mixing chamber (including stir bar). 1 ml of lysis buffer (Zymo Research, Irvine, CA) and 500 µl of sample then was added to the mixing chamber and stir bar rotated using the mixing apparatus as described herein at 3000 rpm for 1 minute. The lysate was collected, bound to a Zymo Research Zymo-Spin IIC-XL column, washed and eluted using standard spin column centrifugation steps. Bench controls using lysis buffer alone, or lysis buffer plus beads, were performed as follows: 500 µl of sample was mixed with 1 mL of lysis buffer. The resulting mixture was then added, or not, to a prefilled tube containing 0.7 mL dry volume of 0.1 & 0.5 mm zirconia beads, attached horizontally to a vortex, and vortexed for 1 minute. The lysate was collected, bound to a Zymo Research Zymo-Spin IIC-XL column, washed and eluted using standard spin column centrifugation procedure.

Figure 9:
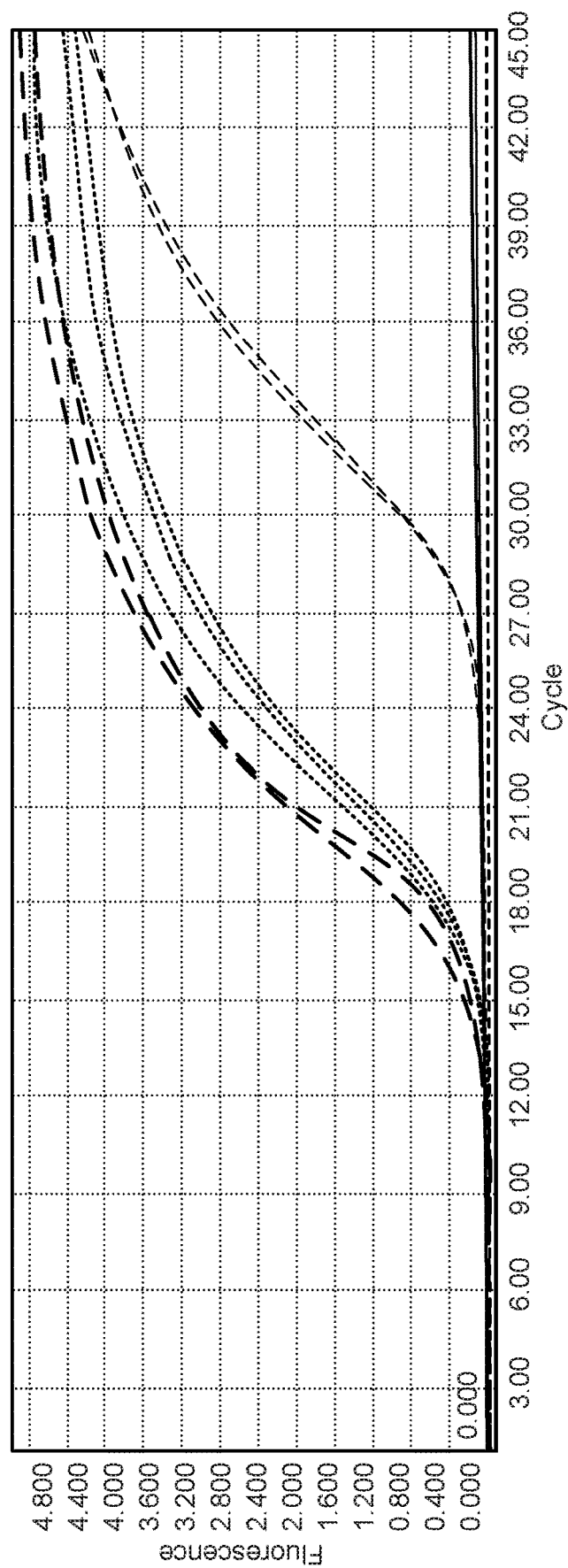
FIG. 9 is a graph depicting DNA amplification curves obtained during performance of qPCR on a sample, following preparation of the sample using different mixing methods: long dash represents the amplification curves for cells mixed at the bench with buffer and beads; medium dashes represents the amplification curves for cells mixed at the bench with lysis buffer only; short dashes represent amplification curves for cells processed with the mixing apparatus containing lysis buffer and beads.

Lysis was evaluated via RT-qPCR. In this example, a 20 µl reaction contained 10 µl of 2× reaction buffer and 0.8 µl enzyme mix, Clontech One Step SYBR Primescript RT-PCR Kit II, 250 nm forward and reverse primers to *C. albicans* 28S ribosomal RNA, 4 µl extracted nucleic acid. The reactions were processed on a Roche LC96 lightcycler with the following protocol: 10 min at 42° C. for reverse transcription, enzyme inactivation at 95° for 10 sec, followed by 45 cycles of denaturation at 95° C. for 20 sec, annealing at 60° C. for 20 sec, extension at 72° for 15 sec. Amplification curves are illustrated in FIG. 9. Specificity of amplification was confirmed by high resolution melting.

TABLE 1

YEAST LYSIS IN MIXING APPARATUS

| Lysis method | Cq ± SD | Wells Detected |
|---|---|---|
| Mixing apparatus: lysis buffer + beads | 16.38 ± 0.1 | 3 of 3 |
| Bench: lysis buffer | 26.76 ± 0.08 | 3 of 3 |
| Bench: lysis buffer + beads | 15.07 ± 0.03 | 3 of 3 |
| Bench: neg. PBS + lysis buffer + beads | no amplification | 0 of 2 |
| no template control | no amplification | 0 of 2 |

Bench extractions with and without bead beating were used as controls and the extractions evaluated via RT-qPCR. The experiment was replication (data not shown) and both iterations showed less than 1 cycle difference in Cq values relative to bench experiments.

The amplification curves depicted in FIG. 9 indicate that approximately the same quantity of the DNA sequence was initially detected when the reaction solution was mixed using the mixing assembly, compared to when the reaction solution was mixed using the vortex mixer and zirconia beads.

FIGURE NUMBERING KEY

| Item | Numbering suffix |
|---|---|
| magnetic mixing apparatus | 00 |
| driving magnet system | 10 |
| first driving magnet | 11 |
| first magnet field focuser | 12 |
| first driving magnet magnetic axis | 13 |
| second driving magnet | 16 |
| second driving magnet field focuser | 17 |
| second driving magnet magnetic axis | 18 |
| driving magnet rotational axis | 20 |
| driving magnet spindle | 21 |
| driving magnet holder/spacer | 25 |
| drive motor | 30 |
| drive belt | 32 |
| mixing assembly holder | 40 |
| driven magnet system | 50 |

-continued

FIGURE NUMBERING KEY

| Item | Numbering suffix |
|---|---|
| first driven magnet | 51 |
| first driven magnet field focuser | 52 |
| first driven magnet magnetic axis | 53 |
| second driven magnet | 56 |
| second driven magnet field focuser | 57 |
| second driven magnet magnetic axis | 58 |
| driven magnet rotational axis | 60 |
| driven magnet spindle | 61 |
| driven magnet holder/spacer | 65 |
| mixing assembly | 70 |
| mixing chamber | 71 |
| bounding surface | 72 |
| center | 73 |
| beads | 74 |
| magnetic field lines | 75 |
| supportive plate | 76 |
| perforations | 77 |
| sample inlet | 81 |
| air channel | 82 |
| sample loading well | 83 |
| chamber loading channel | 85 |
| sample transfer channel | 86 |
| bead filter channels | 87 |
| sample exit channel | 88 |
| stir bar | 90 |
| stir bar rotational axis | 92 |
| largest dimension | 94 |

We claim:

1. A method of lysing a cell contained within a fluid sample, comprising:
   loading the fluid sample into a sample loading well of a mixing assembly;
   applying pneumatic pressure to the sample loading well to advance the sample into a mixing chamber of the mixing assembly;
   energizing a drive motor of a driving magnet system to rotate a drive magnet of the driving magnet system;
   rotating a driven magnet system that is magnetically coupled to the drive magnet of the driving magnetic system while the mixing chamber is within a gap between the driving magnetic system and the driven magnetic system;
   rotating a stir bar located within the mixing chamber, wherein the stir bar is magnetically coupled between the driving magnetic system and the driven magnetic system;
   producing a lysed sample within the mixing chamber by continuing the rotating a stir bar step to mix the fluid sample within the mixing chamber;
   stopping the rotating a stir bar step by de-energizing the drive motor of the driving magnet system; and
   advancing the lysed sample through a filter channel of the mixing chamber into a sample exit channel of the mixing assembly.

2. The method of lysing a cell contained within a fluid sample according to claim 1 further comprising: closing a sample inlet channel in communication with the sample loading well, closing a chamber loading channel in communication with the mixing chamber and closing a sample exit channel in communication with the mixing chamber during the producing a lysed sample step.

3. The method of lysing a cell contained within a fluid sample according to claim 2 further comprising:
   applying pneumatic pressure to the sample loading well during the producing a lysed sample step.

4. The method of lysing a cell contained within a fluid sample according to claim 1, wherein a lysis buffer is within the mixing chamber during the rotating a stir bar step.

5. The method of lysing a cell contained within a fluid sample according to claim 4, wherein a plurality of beads are within the mixing chamber during the rotating a stir bar step.

6. The method of lysing a cell contained within a fluid sample according to claim 1 further comprising a step of: introducing a lysis buffer into the mixing chamber before or after performing the loading the fluid sample into a sample loading well step.

7. The method of lysing a cell contained within a fluid sample according to claim 6, wherein the lysis buffer comprises one or more chemical lysing agents.

8. The method of lysing a cell contained within a fluid sample according to claim 7 the one or more chemical lysing agents selected from the group consisting of hypotonic solutions, solutions containing an organic solvent, a chelating agent, a surfactant, a chaotropic agent and combinations thereof.

9. The method of lysing a cell contained within a fluid sample according to claim 1, wherein the gap between the driving magnetic system and the driven magnetic system is between 10 mm to 30 mm.

10. The method of lysing a cell contained within a fluid sample according to claim 1, wherein a largest dimension of a mixing chamber is 1 mm to 200 mm.

11. The method of lysing a cell contained within a fluid sample according to claim 1, wherein a mixing chamber volume is 0.1 mL to 100 mL.

12. The method of lysing a cell contained within a fluid sample according to claim 11, wherein a stir bar volume is 50 uL to 10 mL.

13. The method of lysing a cell contained within a fluid sample according to claim 1 further comprising detecting decoupling of the stir bar to the driving magnetic system and the driven magnetic system and performing the stopping the rotating a stir bar step in response to the detecting decoupling of the stir bar.

14. The method of lysing a cell contained within a fluid sample according to claim 13, wherein the detecting decoupling of the stir bar is performed using a microphone or an accelerometer.

15. A method of mixing a fluid sample containing a cell within a mixing chamber of a mixing assembly, comprising:
   loading the fluid sample containing the cell into a sample inlet of a sample loading well in communication with the mixing chamber;
   applying pneumatic pressure to the sample loading well to advance the fluid sample from the sample loading well into the mixing chamber;
   rotating a driving magnetic system that is magnetically coupled to a driven magnetic system while the mixing chamber is within a gap between the driving magnetic system and the driven magnetic system;
   mixing the fluid sample within the mixing chamber by rotating a stir bar located within the mixing chamber, wherein the stir bar is magnetically coupled between the driving magnetic system and the driven magnetic system;
   stopping the rotating a driving magnetic system step; and
   applying pneumatic pressure to advance the fluid from the mixing chamber through a filter channel to a sample exit channel.

16. The method of claim 15 further comprising: loading a lysis buffer into the mixing chamber before the loading the fluid sample step.

17. The method of claim 15 further comprising: mixing the fluid sample with a lysis buffer in the mixing chamber during the mixing the fluid sample step.

18. The method of claim 15 wherein the gap between the driving magnetic system and the driven magnetic system is between 10 mm to 30 mm.

19. The method of claim 15 wherein a largest dimension of a mixing chamber volume is 1 mm to 200 mm.

20. The method of claim 15 wherein a mixing chamber volume comprises 0.1 mL to 100 mL.

21. The method of claim 20 wherein a stir bar volume comprises 50 uL to 10 mL.

* * * * *